United States Patent
Chiang et al.

(10) Patent No.: US 11,293,897 B2
(45) Date of Patent: Apr. 5, 2022

(54) HIGH SENSITIVITY ISFET SENSOR

(71) Applicant: Taiwan Semiconductor Manufacturing Co., Ltd., Hsin-Chu (TW)

(72) Inventors: Katherine H. Chiang, New Taipei (TW); Jui-Cheng Huang, Hsinchu (TW); Ke-Wei Su, Zhubei (TW); Tung-Tsun Chen, Hsinchu (TW); Wei Lee, Hsinchu (TW); Pei-Wen Liu, Hsinchu (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 0 days.

(21) Appl. No.: 16/413,865

(22) Filed: May 16, 2019

(65) Prior Publication Data
US 2020/0173958 A1 Jun. 4, 2020

Related U.S. Application Data

(60) Provisional application No. 62/773,474, filed on Nov. 30, 2018.

(51) Int. Cl.
| | |
|---|---|
| *G01N 27/414* | (2006.01) |
| *G01N 33/543* | (2006.01) |
| *G01N 27/02* | (2006.01) |

(52) U.S. Cl.
CPC ......... *G01N 27/4145* (2013.01); *G01N 27/02* (2013.01); *G01N 33/54373* (2013.01)

(58) Field of Classification Search
CPC .............. G01N 27/4145; G01N 27/02; G01N 33/54373; G01N 33/5438; G01N 27/414;
(Continued)

(56) References Cited

U.S. PATENT DOCUMENTS 10,161,901 B2  12/2018 Huang et al.
10,852,271 B2  12/2020 Chen et al.
(Continued)

FOREIGN PATENT DOCUMENTS

KR  20110037283 A  4/2011
TW    201518722 A  5/2015

OTHER PUBLICATIONS

Institute for Microelectronics. "Working Principle of a BioFET." The date of publication is unknown. Retrieved online on Feb. 24, 2019 from http://www.iue.tuwien.ac.at/phd/windbacher/node24.html.

(Continued)

*Primary Examiner* — Melanie Brown
(74) *Attorney, Agent, or Firm* — Eschweiler & Potashnik, LLC

(57) ABSTRACT

Various embodiments of the present application are directed towards an ion-sensitive field-effect transistor for enhanced sensitivity. In some embodiments, a substrate comprises a pair of first source/drain regions and a pair of second source/drain regions. Further, a first gate electrode and a second gate electrode underlie the substrate. The first gate electrode is laterally between the first source/drain regions, and the second gate electrode is laterally between the second source/drain regions. An interconnect structure underlies the substrate and defines conductive paths electrically shorting the second source/drain regions and the second gate electrode together. A passivation layer is over the substrate and defines a first well and a second well. The first and second wells respectively overlie the first and second gate electrodes, and a sensing layer lines the substrate in the first and second wells. In some embodiments, sensing probes are in the first well, but not the second well.

20 Claims, 25 Drawing Sheets

(58) Field of Classification Search
CPC .. G01N 27/4146; G01N 33/48; H01L 27/092; H01L 29/772
See application file for complete search history.

(56) References Cited

U.S. PATENT DOCUMENTS

| | | | |
|---|---|---|---|
| 2006/0011911 | A1 | 1/2006 | Bockelmann et al. |
| 2007/0208243 | A1* | 9/2007 | Gabriel ............... B82Y 15/00 600/347 |
| 2012/0074956 | A1 | 3/2012 | Fife et al. |
| 2013/0273664 | A1 | 10/2013 | Toumazou et al. |
| 2014/0264467 | A1* | 9/2014 | Cheng ............... G01N 27/4148 257/253 |
| 2015/0362458 | A1 | 12/2015 | Yanagawa et al. |
| 2017/0343498 | A1 | 11/2017 | Kalnitsky et al. |
| 2017/0370875 | A1 | 12/2017 | Ono et al. |

OTHER PUBLICATIONS

Vitale et al. "FDSOI Process Technology for Subthreshold-Operation Ultralow-Power Electronics." Proceedings of the IEEE, vol. 98, No. 2, Feb. 2010.

Wikipedia.org "Bio-FET." Published on Dec. 16, 2018. Retrieved online on Feb. 24, 2019 from https://en.wikipedia.org/wiki/Bio-FET.

Estrela, Pedro. "Biologically sensitive field-effect transistors: from ISFETs to NanoFETs." Essays Biochem. Jun. 30, 2016; 60(1): 81-90. Published on Jun. 30, 2016.

Kaisti, Matti. "Detection principles of biological and chemical FET sensors." Biosensors and Bioelectronics vol. 98, Dec. 15, 2017, pp. 437-448.

Electronics Tutorials. "The Differential Amplifier." The date of publication is unknown. Retrieved online on Feb. 20, 2019 from: https://www.electronics-tutorials.ws/opamp/opamp_5.html.

Wikipedia.org "Doping (semiconductor)." Published on Feb. 16, 2019. Retrieved online on Feb. 23, 2019 from: https://en.wikipedia.org/wiki/Doping.

Huang et al. "High Performance Dual-Gate ISFET with Non-ideal Effect Reduction Schemes in a SOI-CMOS Bioelectrical SoC." 2015 IEEE International Electron Devices Meeting (IEDM), published Dec. 2015.

Berkeley EECS. "EE 130. Integrated-Circuit Devices: Lecture #23." Published Spring 2013.

Cauchy et al. "Questions and Answers on Fully Depleted SOI Technology for Next Generation CMOS Nodes." SOI Industry Consortium, published Apr. 2010.

Zeng et al. "A reference-less semiconductor ion sensor." Sensors and Actuators B 254 (2018) 102-109, published on Jun. 23, 2017.

\* cited by examiner

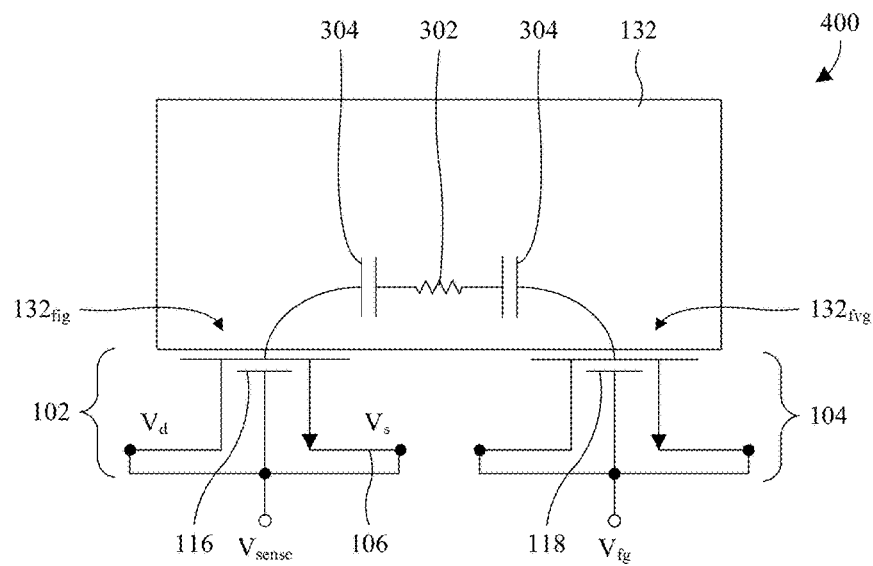
Fig. 4
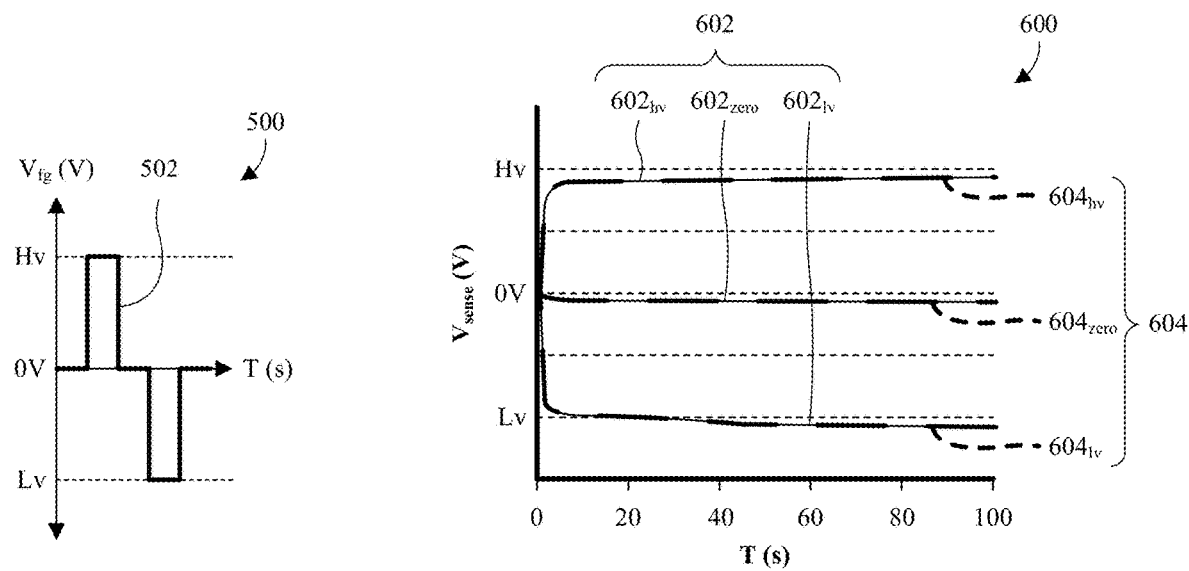
Fig. 5  Fig. 6

HIGH SENSITIVITY ISFET SENSOR

REFERENCE TO RELATED APPLICATION

This application claims the benefit of U.S. Provisional Application No. 62/773,474, filed on Nov. 30, 2018, the contents of which are incorporated herein by reference in their entirety.

BACKGROUND

An ion-sensitive field-effect transistor (ISFET) is a field-effect transistor used for characterizing and/or identifying a target in a fluid. The target reacts with and/or binds to a sensing layer in the fluid to change a surface potential difference at the sensing layer. The change in the surface potential difference changes a threshold voltage of the ISFET, which may be used to characterize and/or identify the target. ISFETs are widely used in different life-science applications, ranging from environmental monitoring and basic life science research to Point-of-Care (PoC) in-vitro molecular diagnostics.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 4 illustrates a circuit diagram of some embodiments of the effective circuit of FIG. 3 during a direct current (DC)/alternating current (AC) potentiometric readout methodology.

FIG. 5 illustrates a graph of some embodiments of a cycle of an AC fluidic-gate voltage used during the DC/AC potentiometric readout methodology of FIG. 4.

FIG. 6 illustrates a graph of some embodiments of sensing results generated using the DC/AC potentiometric readout methodology of FIG. 4.

DETAILED DESCRIPTION

Figure 1:
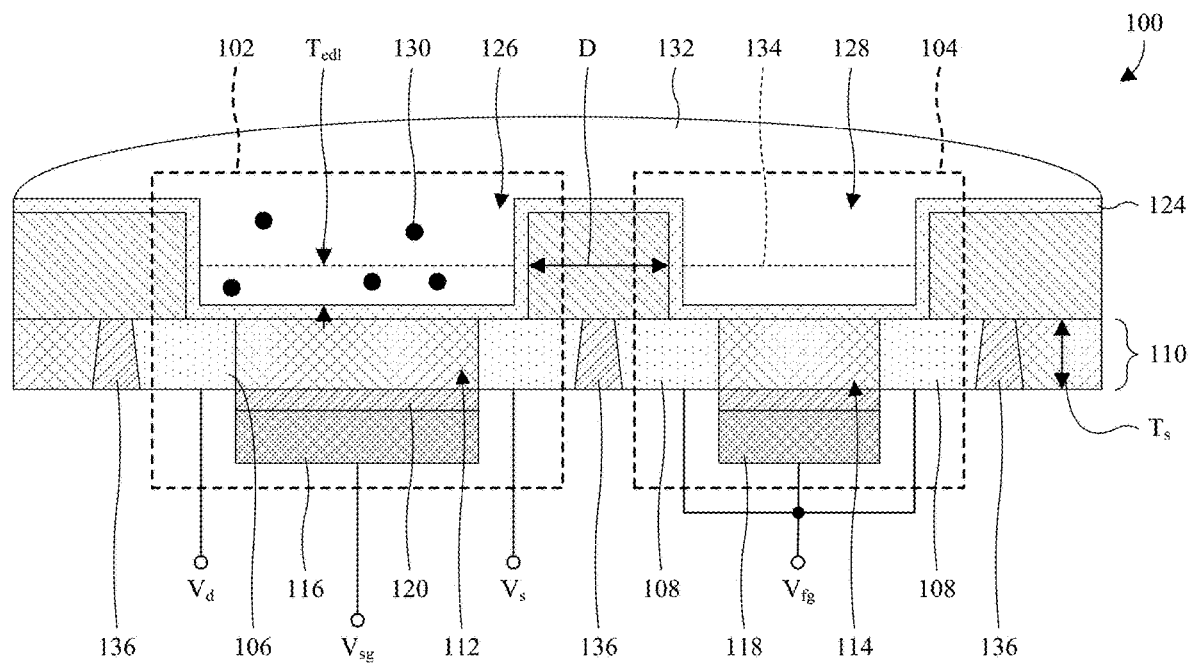
FIG. 1 illustrates a cross-sectional view of some embodiments of a sensor comprising an ion-sensitive field-effect transistor (ISFET) and a voltage-reference field-effect transistor (VRFET).

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

A sensor may, for example, comprise a reference electrode and an ion-sensitive field-effect transistor (ISFET). The ISFET comprises a pair of source/drain regions and a body region. The source/drain regions and the body region are in a substrate and the body region extends between the source/drain regions. Further, the ISFET comprises a sensing layer. The sensing layer is on a sensing side of the substrate and lines the body region. During use of the sensor, a fluid comprising a target is placed on the sensing layer. The target reacts with and/or binds to the sensing layer to change a surface potential difference at the sensing layer. The change in the surface potential difference changes a threshold voltage of the ISFET, which may be used to characterize and/or identify the target. For example, the fluid may be biased with the reference electrode to induce formation of a channel in the body region and the target may be characterized and/or identified by an impedance of the channel.

A challenge with the sensor is that the sensor may be designed to sense targets with a specific polarity. For example, doping types of the ISFET may be tailored to the specific polarity. Hence, a sensor designed to sense targets with a positive polarity has low sensitivity for targets with a negative polarity and vice versa. Another challenge with the sensor is that a distance between a charge center of the target and the sensing layer may be large. Sensitivity is dependent on charge amount of the target and distance between the charge center of the target and the sensing layer. For example, if the charge center of the target is outside an electrical double layer (EDL) of the ISFET, sensitivity may be low. Hence, sensitivity may be low due to the large distance between the charge center and the sensing layer. Another challenge with the sensor is that a distance between the reference electrode and the sensing layer may be large. For example, the reference electrode may be a silver (Ag)/silver chloride (AgCl) electrode. An Ag/AgCl electrode is limited to a relatively large size and cannot be readily scaled down. Further, due to the large size, the Ag/AgCl electrode has a large intrinsic capacitance and cannot be moved into close proximity with the sensing layer. Due to the large intrinsic capacitance and the large distance, high parasitic resistances and/or high parasitic capacitances may lead to a high voltage drop and render it impractical to use alternating current (AC) for sensing. Another challenge with the sensor is that sensitivity may be degraded by the drift effect and the hysteresis effect. The drift effect may pertain to a drift in measurements over time, whereas the hysteresis effect may pertain to hysteresis in measurements when a pH of the fluid is swept up and down. The drift effect and the hysteresis effect may arise when the reference electrode and the ISFET have different structures and hence have EDLs with different thicknesses. The reference electrode and the ISFET may have different structures and hence different EDLs when the reference electrode is an Ag/AgCl electrode.

Various embodiments of the present application are directed towards a high sensitivity ISFET sensor. In some embodiments, the sensor comprises an ISFET and a voltage-reference field-effect transistor (VRFET). A substrate comprises a pair of ISFET source/drain regions and a pair of VRFET source/drain regions. A solid ISFET gate electrode and a solid VRFET gate electrode underlie the substrate. The solid ISFET gate electrode is laterally between the ISFET source/drain regions, and the solid VRFET gate electrode is laterally between the VRFET source/drain regions. An interconnect structure underlies the substrate and electrically couples the VRFET source/drain regions and the solid VRFET gate electrode to each other. A passivation layer overlies the substrate and defines an ISFET well and a VRFET well. The ISFET and VRFET wells respectively overlie the solid ISFET and VRFET gate electrodes and a sensing layer lines the substrate in the ISFET and VRFET wells. The ISFET source/drain regions, the solid ISFET gate electrode, and a portion of the sensing layer in the ISFET well partially define the ISFET. The VRFET source/drain regions, the solid VRFET gate electrode, and a portion of the sensing layer in the VRFET well partially define the VRFET.

During use of the sensor, the VRFET serves as a reference electrode for the ISFET. By using the VRFET as the reference electrode, the ISFET and the reference electrode may have the same structure and may hence have EDLs with the same thickness. Due to EDLs with the same thickness, the drift and hysteresis effects are reduced and hence the sensor has high sensitivity and high accuracy. Additionally, by using the VRFET as the reference electrode, a distance between the ISFET and the reference electrode may be small. For example, the VRFET may be formed with the ISFET using semiconductor manufacturing processes and hence may be scaled down and located in close proximity to the ISFET. Due to the small distance between the ISFET and the reference electrode, parasitic resistances, parasitic capacitances, and voltage drops between the ISFET and the reference electrode are low. As a result, the sensor has high sensitivity and high accuracy. Further, multiple different readout methodologies that may not otherwise be available may be used to characterize and/or identify the target.

With reference to FIG. 1, a cross-sectional view 100 of some embodiments of a sensor comprising an ISFET 102 and a VRFET 104 is provided. A pair of ISFET source/drain regions 106 and a pair of VRFET source/drain regions 108 are in a substrate 110. The ISFET source/drain regions 106 share a common doping type (e.g., p-type or n-type) and are on opposite sides of an ISFET body region 112 in the substrate 110. Similarly, the VRFET source/drain regions 108 share a common doping type and are on opposite sides of a VRFET body region 114 in the substrate 110. The substrate 110 may be, for example, a bulk silicon substrate and/or some other suitable semiconductor substrate.

A solid ISFET gate electrode 116 and a solid VRFET gate electrode 118 are on a frontside of the substrate 110, respectively at the ISFET and VRFET body regions 112, 114, and are spaced from the substrate 110 by individual gate dielectric layers 120. The solid ISFET and VRFET gate electrodes 116, 118 may be or comprise, for example, doped polysilicon and/or some other suitable conductive material(s). The gate dielectric layers 120 may be or comprise, for example, silicon oxide and/or some other suitable dielectric(s).

A passivation layer 122 and a sensing layer 124 are on a backside of the substrate 110, opposite the frontside of the substrate 110. The passivation layer 122 defines an ISFET well 126 and a VRFET well 128 respectively at the ISFET and VRFET body regions 112, 114. The passivation layer 122 may be or comprise, for example, silicon oxide and/or some other suitable dielectric(s). The sensing layer 124 lines the ISFET and VRFET body regions 112, 114 in the ISFET and VRFET wells 126, 128 and is configured to react with or otherwise bind to a target 130 to change a surface potential difference of the sensing layer 124. The target 130 is in a fluid 132 on the backside of the substrate 110 and may be or comprise, for example, ions, nucleic acids, polarized molecules, antigens, antibodies, enzymes, cells, some other suitable target(s), or any combination of the foregoing.

In some embodiments, the sensing layer 124 binds directly to the target 130. In other embodiments, the sensing layer 124 binds indirectly to the target 130 through sensing probes (not shown) on the sensing layer 124. In some embodiments, the sensing layer 124 is or comprises hafnium oxide, tantalum oxide, zirconium oxide, some other suitable high k dielectric(s), or any combination of the foregoing. In some embodiments, the sensing layer 124 is sensitive to a pH of the fluid 132 and hence reacts to a pH of the fluid 132 to change a surface potential difference at the sensing layer 124. For example, the sensing layer 124 may be or comprise hafnium oxide and/or some other suitable sensing material(s).

The ISFET source/drain regions 106, the ISFET body region 112, the solid ISFET gate electrode 116, and a portion of the sensing layer 124 in the ISFET well 126 at least partially define the ISFET 102. The VRFET source/drain regions 108, the VRFET body region 114, the solid VRFET gate electrode 118, and a portion of the sensing layer 124 in the VRFET well 128 at least partially define the VRFET 104. The ISFET 102 and the VRFET 104 neighbor on the substrate 110 and the VRFET 104 serves as a reference electrode for the ISFET 102. The ISFET 102 and the VRFET 104 may, for example, be or be part of an integrated chip and/or some other suitable semiconductor structure(s).

During use of the sensor, the fluid 132 serves as an additional gate electrode for the ISFET 102 (i.e., a fluidic ISFET gate electrode) and the sensing layer 124 binds to or otherwise reacts with the target 130 to change a surface potential difference at the sensing layer 124. The surface potential difference, in turn, changes a threshold voltage of the fluidic ISFET gate electrode. Further, due to capacitive coupling between the fluidic ISFET gate electrode and the solid ISFET gate electrode 116, a threshold voltage of the solid ISFET gate electrode 116 also changes. Threshold-voltage variations may, in turn, be used to characterize and/or identify the target 130 by an AC impedance readout methodology, a DC/AC potentiometric readout methodology, and other suitable readout methodologies.

In some embodiments, the ISFET source/drain regions 106 are respectively biased at a drain voltage $V_d$ and a source voltage $V_s$. Further, the fluidic ISFET gate electrode is biased at a fluidic-gate voltage $V_{fg}$ that is at or above a corresponding threshold voltage and/or the solid ISFET gate electrode 116 is biased at a solid-gate voltage $V_{sg}$ that is at or above a corresponding threshold voltage. For example, the source voltage $V_s$ may be about 0 volts, the drain voltage $V_d$ may be about 0.2 volts, the fluidic-gate voltage $V_{fg}$ may be about 0 volts, and the solid-gate voltage $V_{sg}$ may be about 0.5 volts. The biasing causes a channel (not shown) to form in the ISFET body region 112 and threshold voltage variations from the target 130 cause variations in an impedance of the channel. Hence, the impedance of the channel and/or drain current through the channel may be measured to characterize and/or identify the target 130.

The ISFET 102 and the VRFET 104 share a similar structure except that the VRFET source/drain regions 108 and the solid VRFET gate electrode 118 are electrically coupled together while the ISFET source/drain regions 106 and the solid ISFET gate electrode 116 are not electrically coupled together. Because the ISFET 102 and the VRFET 104 share a similar structure, the ISFET 102 and the VRFET 104 have individual EDLs 134 with the same or substantially the same thicknesses $T_{edl}$. Further, because the EDLs 134 have the same or substantially the same thicknesses $T_{edl}$, the drift and hysteresis effects are reduced and hence the sensor has high sensitivity and high accuracy. The drift effect may pertain to a drift in measurements (e.g., channel-impedance measurements) over time. The hysteresis effect may pertain to hysteresis in measurements when a pH of the fluid 132 is swept up and down.

As seen hereafter, the ISFET 102 and the VRFET 104 are formed together using semiconductor manufacturing processes. Hence, the ISFET 102 and the VRFET 104 may be scaled down and located in close proximity to each other. For example, a distance D between the ISFET 102 and the VRFET 104 may be small, such as about 0.1-100.0 micrometers, about 0.1-50.0 micrometers, about 50.0-100.0 micrometers, or other suitable values.

Because of the small distance between the ISFET 102 and the VRFET 104, parasitic resistances, parasitic capacitances, and voltage drops between the ISFET 102 and the VRFET 104 are low. As a result, the sensor has high sensitivity and high accuracy. Further, multiple different readout methodologies may be used to characterize and/or identify the target 130. Amongst these different readout methodologies are an AC impedance readout methodology, a DC/AC potentiometric readout methodology, and a transient/random telegraph signal (RTS)/pulse/noise readout methodology.

In some embodiments, a trench isolation structure 136 extends through the substrate 110 to electrically isolate the ISFET 102 from the VRFET 104. The trench isolation structure 136 comprises silicon oxide and/or some other suitable dielectric(s). The trench isolation structure 136 may be or comprise, for example, a shallow trench isolation (STI) structure, a deep trench isolation (DTI) structure, or some other suitable trench isolation structure.

In some embodiments, the ISFET and VRFET body regions 112, 114 are p-type, whereas the ISFET and VRFET source/drain regions 106, 108 are n-type. In such embodiments, the ISFET 102 and the VRFET 104 are n-channel FETs and have high sensitivity for detecting the target 130 when it has a positive polarity. This follows because bias voltages applied to the fluidic ISFET gate electrode may, for example, be positive and may hence electrostatically repel the target 130 towards the ISFET 102. In other embodiments, the ISFET and VRFET body regions 112, 114 are n-type, whereas the ISFET and VRFET source/drain regions 106, 108 are p-type. In such embodiments, the ISFET 102 and the VRFET 104 are p-channel FETs and have high sensitivity for detecting the target 130 when it has a negative polarity. This follows because bias voltages applied to the fluidic ISFET gate electrode may, for example, be negative and may hence electrostatically repel the target 130 towards the ISFET 102.

In some embodiments, the ISFET and VRFET body regions 112, 114 are fully depleted, such that a depletion region extends completely through a thickness $T_s$ of the substrate 110. The thickness $T_s$ of the substrate 110 may, for example, be about 10-25 nanometers, less than about 25 nanometers, less than about 10 nanometers, or some other suitable value. In some embodiments, the ISFET and VRFET body regions 112, 114 are lightly doped and/or undoped. Light doping may, for example, be less than about $5 \times 10^{15}$ atoms per cubic centimeter ($cm^{-3}$) or some other suitable value. Where the ISFET and VRFET body regions 112, 114 are fully depleted, and/or are lightly doped or undoped, parasitic capacitances and resistances are reduced. This, in turn, enhances sensitivity and accuracy.

Figure 2A:
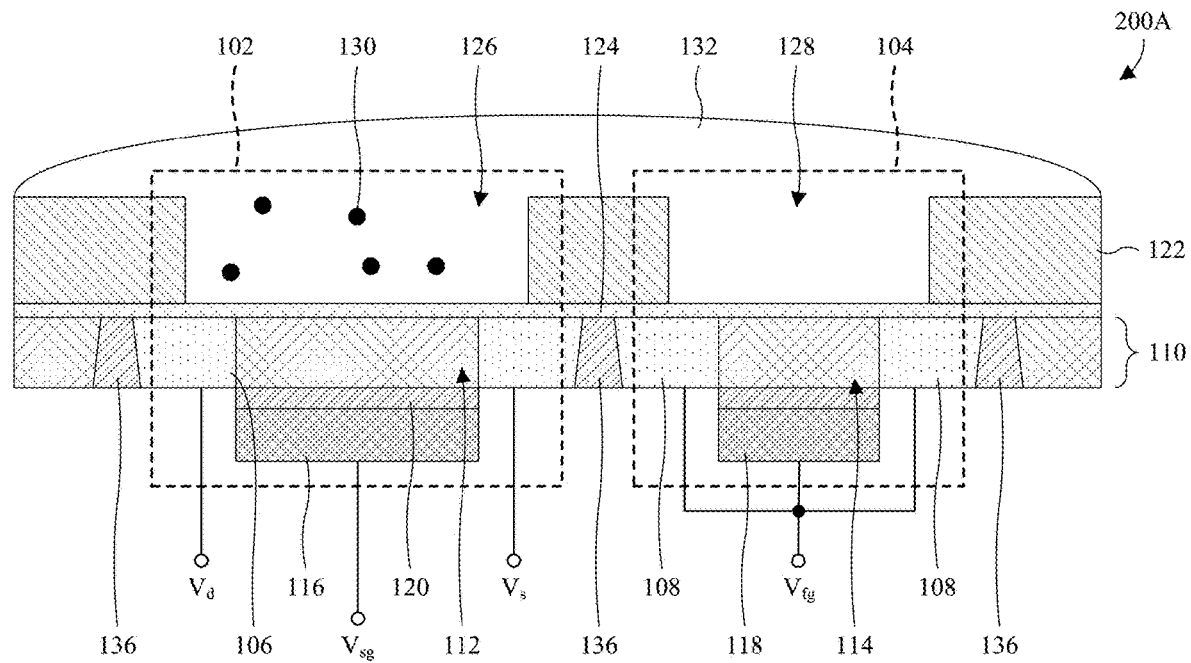
FIGS. 2A-2F illustrate cross-sectional views of some alternative embodiments of the sensor of FIG. 1.

With reference to FIG. 2A, a cross-sectional view 200A of some alternative embodiments of the sensor of FIG. 1 is provided in which the passivation layer 122 overlies the sensing layer 124.

Figure 2B:
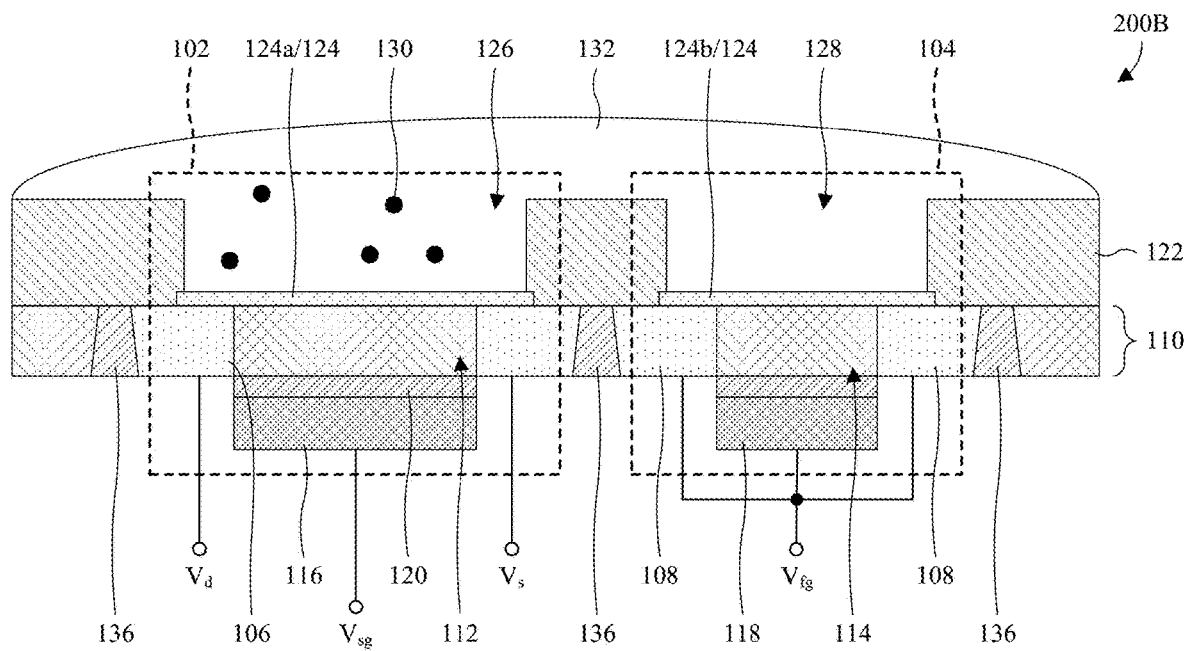

With reference to FIG. 2B, a cross-sectional view 200B of some alternative embodiments of the sensor of FIG. 2A is provided in which the sensing layer 124 has a pair of sensing segments 124a, 124b. The sensing segments 124a, 124b are individual to the ISFET 102 and the VRFET 104 and respectively line the ISFET and VRFET body regions 112, 114.

Figure 2C:
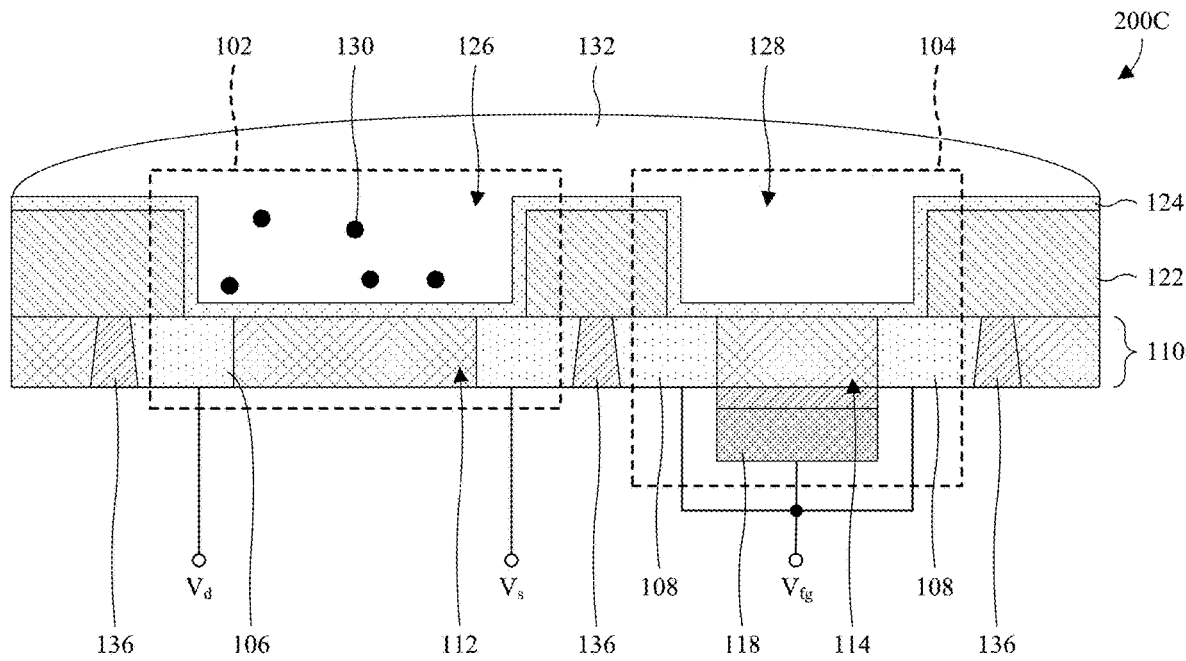

With reference to FIG. 2C, a cross-sectional view 200C of some alternative embodiments of the sensor of FIG. 1 is provided in which the solid ISFET gate electrode 116 and its corresponding gate dielectric layer are omitted.

Figure 2D:
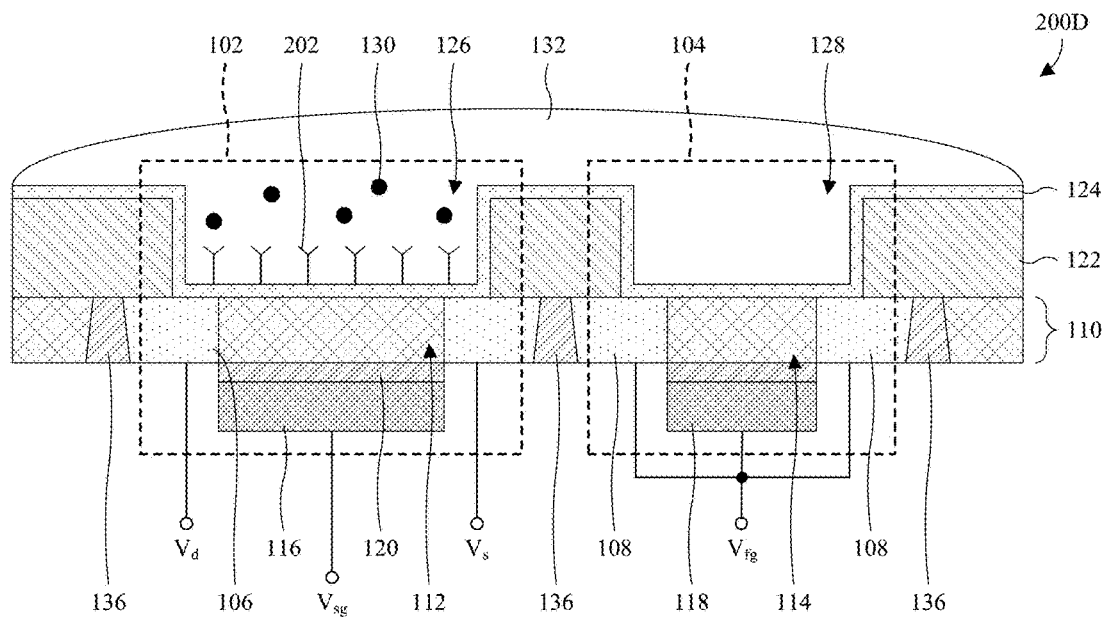

With reference to FIG. 2D, a cross-sectional view 200D of some alternative embodiments of the sensor of FIG. 1 is provided in which a plurality of sensing probes 202 is on the sensing layer 124. The sensing probes 202 are in the ISFET well 126, but not the VRFET well 128. Further, the sensing probes 202 selectively bind with the target 130 to allow selective sensing of the target 130. Selective binding may, for example, mean that the sensing probes 202 bind to the target 130 but no other targets. In some embodiments (as illustrated), the sensing probes 202 are or comprise antibodies. In alternative embodiments, the sensing probes 202 are or comprise nucleic acids, enzymes, or other suitable bio-recognition elements.

Figure 2E:
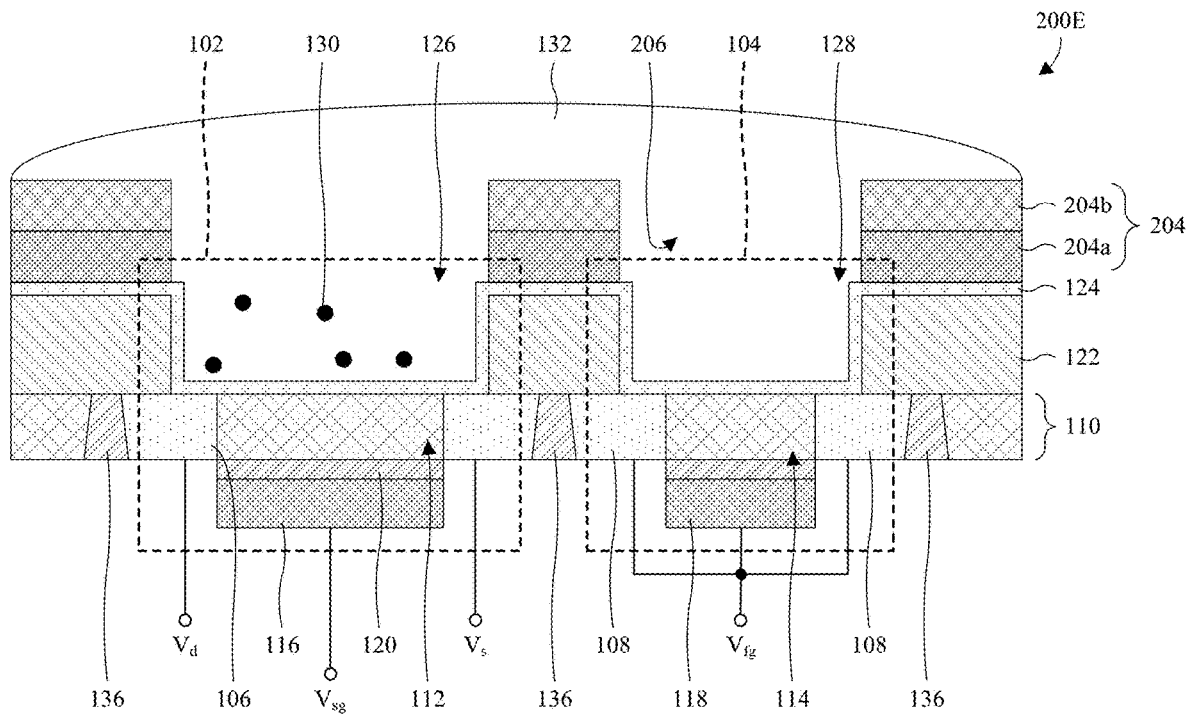

With reference to FIG. 2E, a cross-sectional view 200E of some alternative embodiments of the sensor of FIG. 1 is provided in which a fluidic channel structure 204 is formed on the sensing layer 124. The fluidic channel structure 204 defines fluidic channels 206 individual to and respectively over the ISFET and VRFET wells 126, 128. The fluidic channel structure 204 may be or comprise, for example, polydimethylsiloxane (PDMS), poly(methyl methacrylate) (PMMA), some other suitable material(s), or any combination of the foregoing. In some embodiments, the fluidic channel structure 204 comprises a PDMS layer 204a and a PMMA layer 204b overlying the PDMS layer 204a.

Figure 2F:
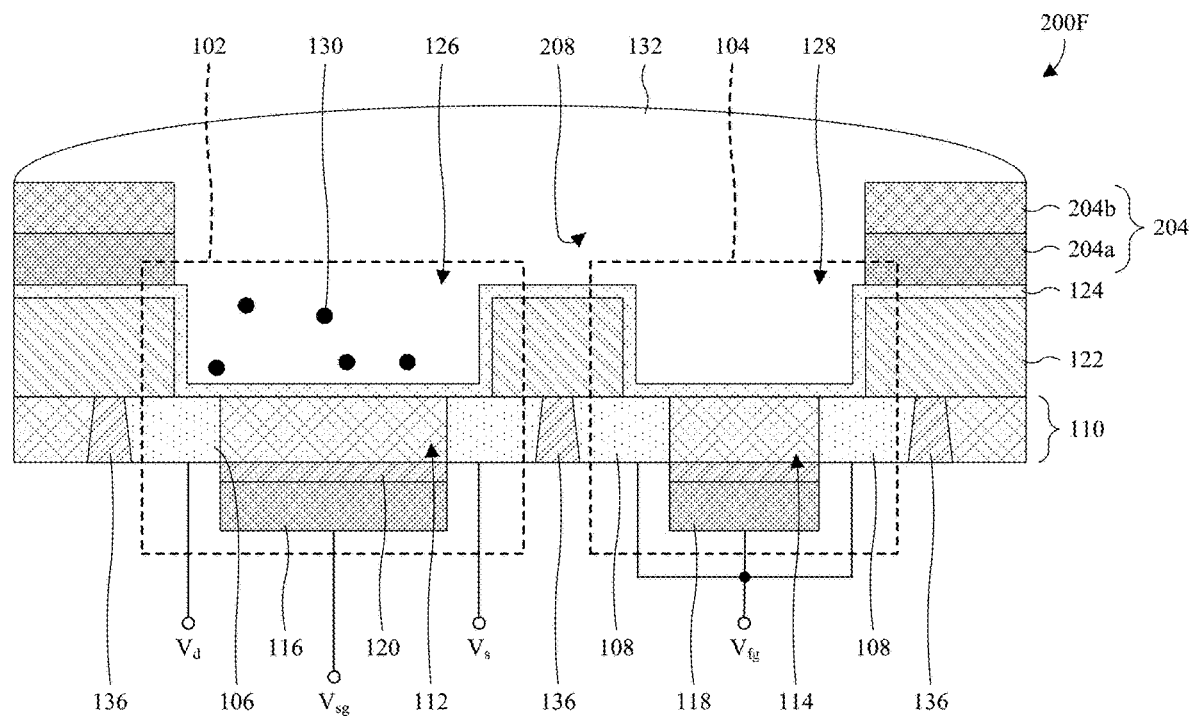

With reference to FIG. 2F, a cross-sectional view 200F of some alternative embodiments of the sensor of FIG. 2E is provided in which the fluidic channel structure 204 defines a fluidic channel 208 shared by the ISFET 102 and the VRFET 104.

While the sensors of FIGS. 2A-2D are illustrated without the fluidic channel structures 204 of FIGS. 2E and 2F, alternative embodiments of the sensors of FIGS. 2A-2D may include the fluidic channel structure 204 in any one of FIGS. 2E and 2F. While FIG. 2D illustrates alternative embodiments of the sensor of FIG. 1 in which the sensor includes the sensing probes 202, alternative embodiments of the sensors of FIGS. 2A-2C, 2E, and 2F may also include the sensing probes 202 of FIG. 2D. While FIG. 2C illustrates embodiments of the sensor of FIG. 1 in which the solid ISFET gate electrode 116 is omitted, alternative embodiments of the sensors of FIGS. 2A, 2B, 2D, 2E, and 2F may also omit the solid ISFET gate electrode 116. While the sensors of FIGS. 1 and 2A-2F are illustrated with the sensing layer 124, alternative embodiments of the sensors may omit the sensing layer 124.

Figure 3:
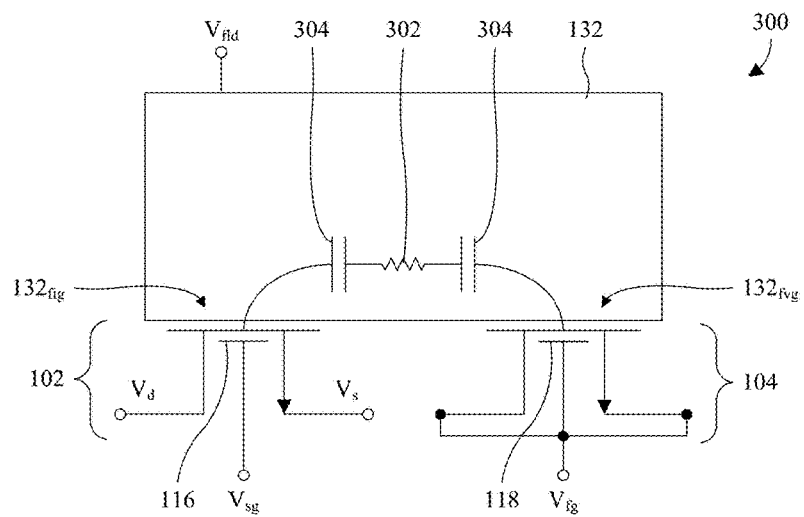
FIG. 3 illustrates a circuit diagram of some embodiments of an effective circuit for the sensor of FIG. 1.

With reference to FIG. 3, a circuit diagram 300 of some embodiments of an effective circuit for the sensor of FIG. 1 is provided. The fluid 132 defines a fluidic ISFET gate electrode $132_{fig}$ of the ISFET 102 and a fluidic VRFET gate electrode $132_{fvg}$ of the VRFET 104. Further, the fluid 132 defines a plurality of parasitic elements between the fluidic ISFET and VRFET gate electrodes $132_{fig}$, $132_{fvg}$. The plurality of parasitic elements includes a parasitic resistor 302 and a pair of parasitic capacitors 304. The parasitic resistor 302 is between and electrically coupled to the parasitic capacitors 304. The parasitic capacitors 304 are respectively at and electrically coupled to the fluidic ISFET and VRFET gate electrodes $132_{fig}$, $132_{fvg}$.

Because of the parasitic capacitors 304 of the fluid 132 and parasitic capacitors (not shown) of the ISFET 102 and the VRFET 104, a fluidic-gate voltage $V_{fg}$ at the VRFET 104 is similar to a fluid voltage $V_{fld}$ at the fluid 132 and the fluid voltage $V_{fld}$ is similar to a solid-gate voltage $V_{sg}$ at the solid ISFET gate electrode 116. As a result, the sensor may, for example, be suited for AC sensing (discussed hereafter).

With reference to FIG. 4, a circuit diagram 400 of some embodiments of the effective circuit of FIG. 3 during a DC/AC potentiometric readout methodology is provided. The ISFET source/drain regions 106 and the solid ISFET gate electrode 116 are electrically coupled together. Further, the fluidic ISFET gate electrode $132_{fig}$ is biased at a fluidic-gate voltage $V_{fg}$ through the VRFET 104. In some embodiments, the fluidic-gate voltage $V_{fg}$ is DC. In other embodiments, the fluidic-gate voltage $V_{fg}$ is AC. The biasing induces a sense voltage $V_{sense}$ at the ISFET source/drain regions 106 and the solid ISFET gate electrode 116 due to capacitive coupling. Further, surface potential differences at the sensing surface of the ISFET 102 cause variations in the sense voltage $V_{sense}$. Such variations in the surface potential difference may, for example, be due to different targets, different target concentrations, etc. Hence, the sense voltage $V_{sense}$ may be used to characterize and/or identify a target.

With reference to FIG. 5, a graph 500 of some embodiments of a cycle 502 of an AC fluidic-gate voltage $V_{fg}$ used during the DC/AC potentiometric readout methodology of FIG. 4 is provided. The lateral axis of the graph 500 corresponds to time, whereas the vertical axis of the graph 500 corresponds to voltage. As seen, the AC fluidic-gate voltage $V_{fg}$ alternatives over time between a high voltage Hv and a low voltage Lv.

With reference to FIG. 6, a graph 600 of some embodiments of sensing results generated using the DC/AC potentiometric readout methodology of FIG. 4 is provided. The lateral axis of the graph 600 corresponds to time, whereas the vertical axis of the graph 600 corresponds to the sense voltage $V_{sense}$. The sense voltage $V_{sense}$ is measured while the fluidic ISFET gate electrode $132_{fig}$ is biased with the AC fluidic-gate voltage $V_{fg}$ of FIG. 5. Further, the sensing layer 124 (see, e.g., FIG. 1) is sensitive to a pH of the fluid 132, whereby a surface potential difference at the sensing layer 124 changes based on the pH. For example, the sensing layer 124 may be hafnium oxide or some other suitable material.

A plurality of first-pH curves 602 and a plurality of second-pH curves 604 describe the sense voltage $V_{sense}$ over time for different values of the AC fluidic-gate voltage $V_{fg}$ of FIG. 5. The plurality of first-pH curves 602 corresponds to a first pH and includes a high-voltage curve $602_{hv}$, a zero-voltage curve $602_{zero}$, and a low-voltage curve $602_{lv}$ that describe measurements while the AC fluidic-gate voltage $V_{fg}$ of FIG. 5 is respectively at the high voltage Hv, zero volts, and the low voltage Lv. Similarly, the plurality of second-pH curves 604 corresponds to a second pH and includes a high-voltage curve $604_{hv}$, a zero-voltage curve $604_{zero}$, and a low-voltage curve $604_{lv}$ that describe measurements while the AC fluidic-gate voltage $V_{fg}$ of FIG. 5 is respectively at the high voltage Hv, zero volts, and the low voltage Lv. As seen, the sense voltage $V_{sense}$ is quick to reach steady state, whereby the sensing frequency may be high. Further, the sense voltage $V_{sense}$ is independent of pH and electrical coupling between the sense voltage $V_{sense}$ and the fluidic-gate voltage $V_{fg}$ is approximately 1:1.

The sense voltage $V_{sense}$ is independent of pH, despite the sensing layer 124 (see, e.g., FIG. 1) being sensitive to pH, because the ISFET 102 and the VRFET 104 have the same or similar structures. The pH of the fluid 132 induces the same surface potential shift at the ISFET 102 as at the VRFET 104, whereby the effect of pH is cancelled. Hence, the surface potential difference at the ISFET 102 is dominated by a target being sensed and not by pH of the fluid 132. Further, the sensor has high sensitivity and high accuracy for the target.

Figure 7:
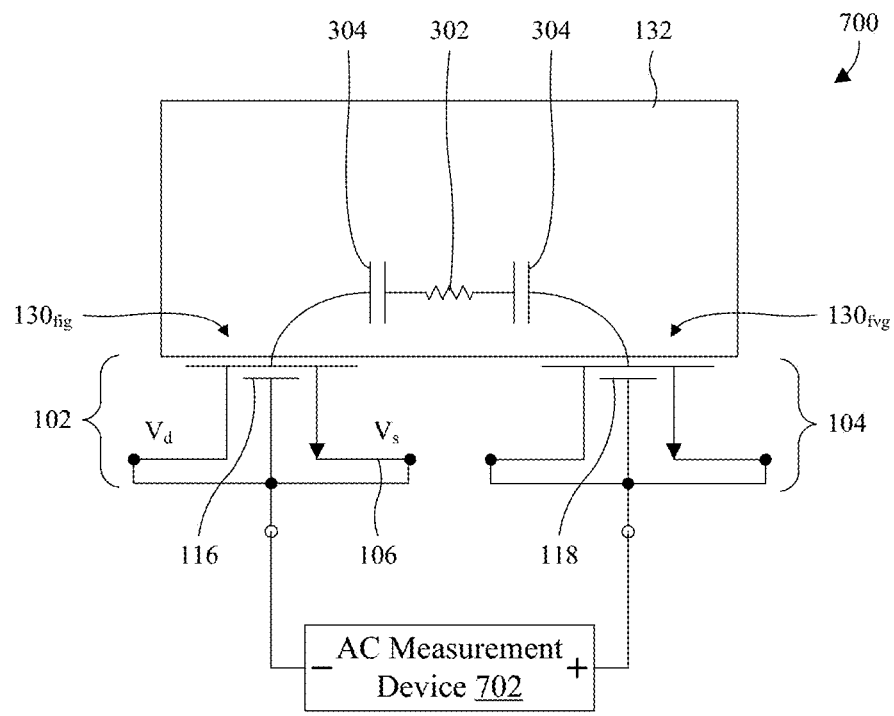
FIG. 7 illustrates a circuit diagram of some embodiments of the effective circuit of FIG. 3 during an AC readout methodology.

With reference to FIG. 7, a circuit diagram 700 of some embodiments of the effective circuit of FIG. 3 during an AC readout methodology is provided. The ISFET source/drain regions 106 and the solid ISFET gate electrode 116 are electrically coupled together. Further, an anode of an AC measurement device 702 is electrically coupled to the VRFET 104, whereas a cathode of the AC measurement device 702 is electrically coupled to the ISFET 102. In alternative embodiments, this electrically coupling is reversed. The AC measurement device 702 is configured to measure capacitance, impedance, and conductance using an AC signal applied to the fluid 132 through the VRFET 104. Capacitance, impedance, and conductance vary due to surface potential differences at the sensing surface of the ISFET 102. Such variations in the surface potential difference may, for example, be due to different targets, different target concentrations, etc. Hence, the capacitance, impedance, conductance, or any combination of the foregoing may be used to characterize and/or identify a target.

Figure 8A:
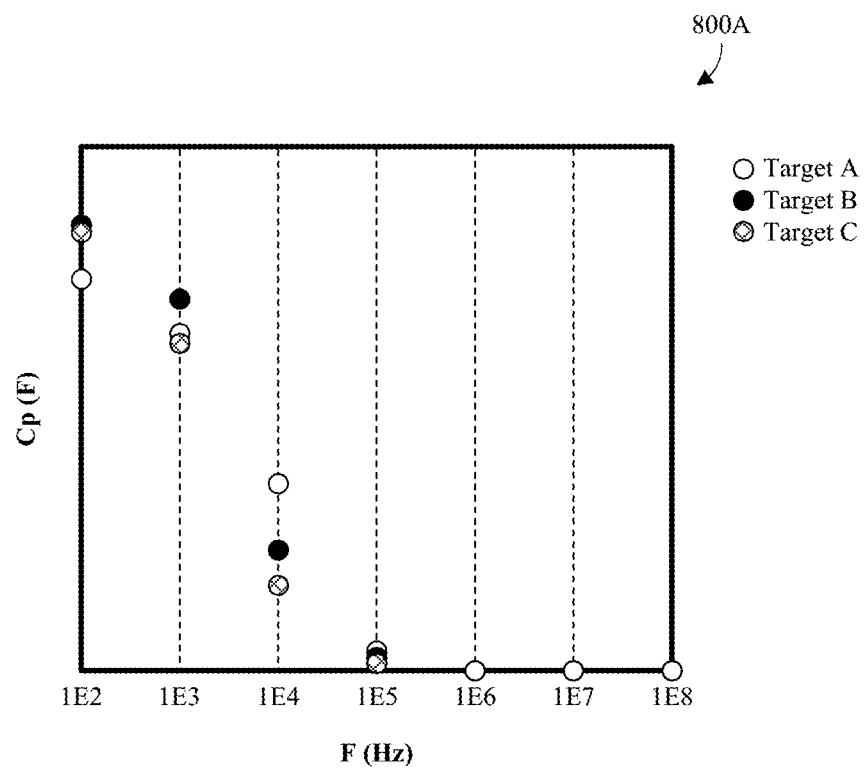
FIGS. 8A-8D illustrate graphs of some embodiments of sensing results generated using the AC readout methodology of FIG. 7.

With reference to FIG. 8A, a graph 800A of some embodiments of capacitance sensing results generated using the AC methodology of FIG. 7 is provided. The lateral axis of the graph 800A is logarithm and corresponds to the frequency of the AC signal. The vertical axis of the graph 800A is linear and corresponds to capacitance from the solid VRFET gate electrode 118 to the solid ISFET gate electrode 116. Capacitance is measured for different targets while the pH of the fluid 132 is constant and frequency is varied. The different targets include Target A, Target B, and Target C and are schematically illustrated with different hashes. As seen, the capacitance for a given frequency varies amongst the different targets, such that the targets may be distinguished from each other based upon capacitance.

Figure 8B:
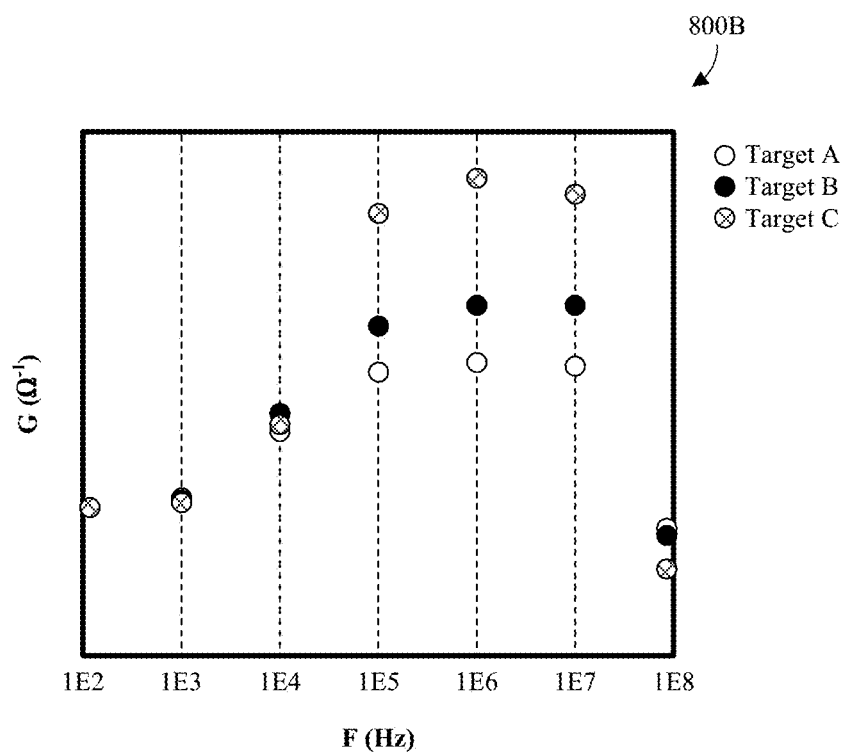

With reference to FIG. 8B, a graph 800B of some alternative embodiments of the graph 800A of FIG. 8A is provided in which conductance sensing results are used in place of capacitance sensing results. Hence, the vertical axis of the graph 800B is linear and corresponds to conductance from the solid VRFET gate electrode 118 to the solid ISFET gate electrode 116. As seen, the conductance for a given frequency varies amongst the different targets, such that the targets may be distinguished from each other based upon conductance.

Figure 8C:
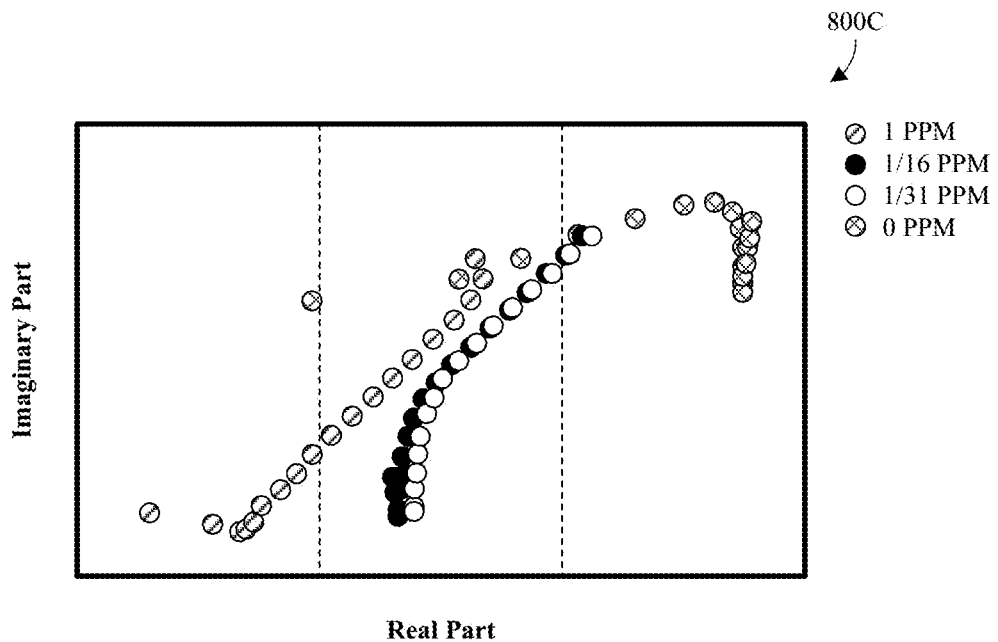

With reference to FIG. 8C, a graph 800C of some embodiments of impedance sensing results generated using the AC methodology of FIG. 7 is provided. The lateral axis of the graph 800C is logarithm and corresponds to the real part of impedance measurements. The vertical axis of the graph 800C is logarithm and corresponds to the imaginary part of impedance measurements. Impedance is measured for different concentrations of a target while the frequency of the AC signal is varied. The different target concentrations include 1 parts per million (PPM), 1/16 PPM, 1/31 PPM, and 0 PPM and are schematically illustrated with different hashes. The target may, for example, be sodium chloride or some other suitable target. As seen, impedance changes for difference target concentrations, such that different target concentrations may be distinguished from each other based upon impedance.

Figure 8D:
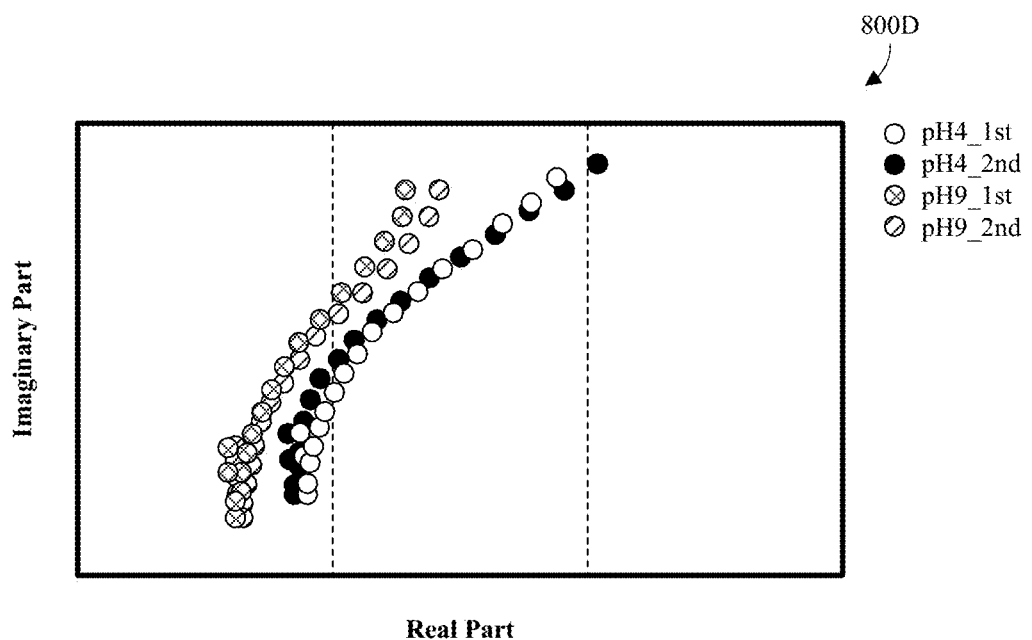

With reference to FIG. 8D, a graph 800D of some embodiments of impedance sensing results generated using the AC methodology of FIG. 7 is provided in which impedance measurements are collected twice for each of two fluids. The lateral axis of the graph 800D is logarithm and corresponds to the real part of impedance measurements. The vertical axis of the graph 800D is logarithm and corresponds to the imaginary part of impedance measurements. The two fluids have different pHs and impedance is measured twice for each of the two fluids by varying the frequency of the AC signal. The differences between the impedance measurements are schematically illustrated with different hashes. As seen, impedance changes for difference pHs, such that different pHs may be distinguished from each other based upon impedance. Further, the impedance measurements for a given fluid are repeatable.

Figure 9:
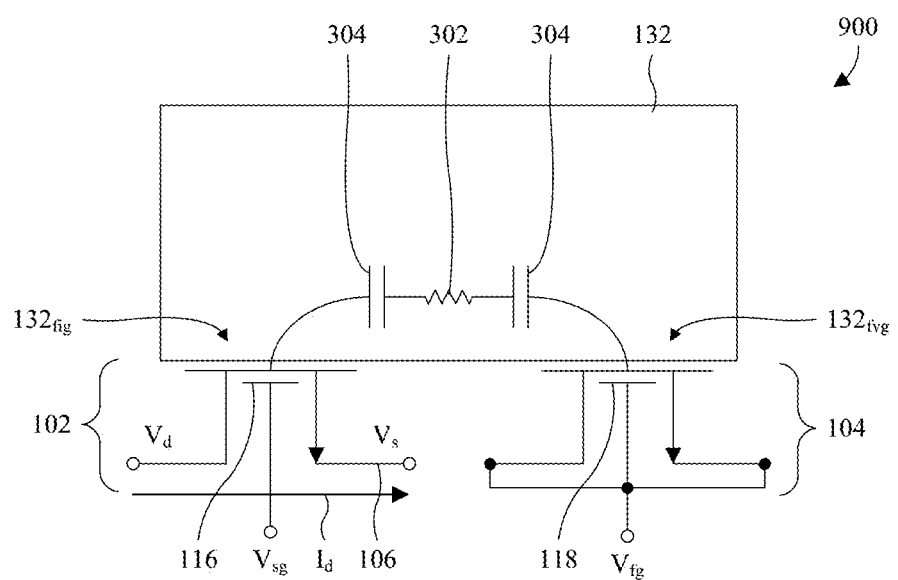
FIG. 9 illustrates a circuit diagram of some embodiments of the effective circuit of FIG. 3 during a transient/random telegraph signal (RTS)/pulse/noise readout methodology.

With reference to FIG. 9, a circuit diagram 900 of some embodiments of the effective circuit of FIG. 3 during a transient/RTS/pulse/noise readout methodology is provided. The ISFET source/drain regions 106 are respectively biased at a drain voltage $V_d$ and a source voltage $V_s$. Further, the solid ISFET gate electrode 116 is based at a solid-gate voltage $V_{sg}$ and the fluidic ISFET gate electrode $132_{fg}$ is biased at a fluidic-gate voltage $V_{fg}$ through the VRFET 104. In some embodiments, the fluidic-gate voltage $V_{fg}$ is DC. In other embodiments, the fluidic-gate voltage $V_{fg}$ is AC. In some embodiments, the fluidic-gate voltage $V_{fg}$ is as illustrated in FIG. 5. The biasing induces drain current $I_d$ to flow through the ISFET 102. Further, variations in surface potential differences at the sensing surface of the ISFET 102 cause variations in the drain current $I_d$. Such variations in the surface potential difference may, for example, be due to different targets, different target concentrations, etc. Hence, the drain current $I_d$ may be used to characterize and/or identify a target.

During a transient readout methodology, a change in the drain current $I_d$ in response to a transition in the fluidic-gate voltage $V_{fg}$ is used to characterize and/or identify the target. The transition may, for example, be a high to low transition, a low to high transition, or some other suitable transition. During a RTS readout methodology, a change in the drain current $I_d$ in response to a DC fluidic-gate voltage $V_{fg}$ (i.e., a constant fluidic-gate voltage $V_{fg}$) is used to characterize and/or identify the target. During a pulse readout methodology, a change in the drain current $I_d$ in response to a pulse in the fluidic-gate voltage $V_{fg}$ is used to characterize and/or identify the target. During a noise readout methodology, the drain current $I_d$ is transformed to the frequency domain using a Fast Fourier Transform (FFT) while the fluidic-gate voltage $V_{fg}$ is constant. The resulting waveform is then used to characterize and/or identify a target.

Figure 10:
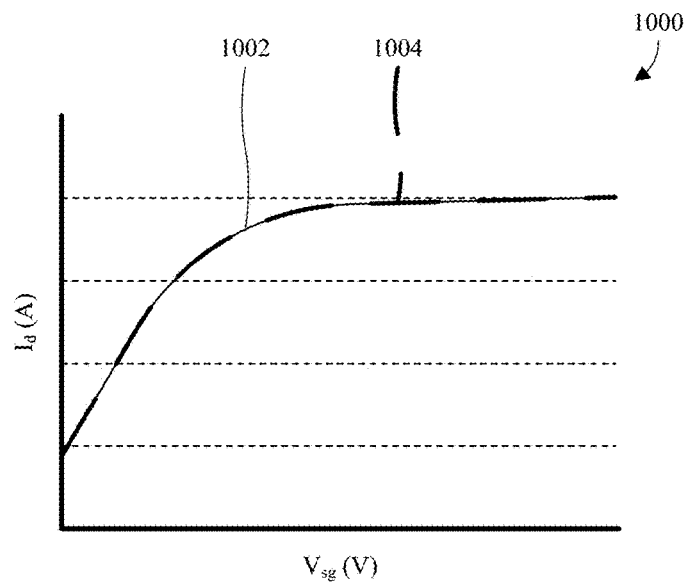
FIG. 10 illustrates a graph of some embodiments of sensing results generated using the transient/RTS/pulse/noise readout methodology of FIG. 9.

With reference to FIG. 10, a graph 1000 of some embodiments of drain current sensing results generated during the transient/RTS/pulse/noise readout methodology of FIG. 9 is provided. The lateral axis of the graph 1000 is linear and corresponds to the solid-gate voltage $V_{sg}$, whereas the vertical axis of the graph 1000 is logarithmic and corresponds to the drain current $I_d$. The drain current $I_d$ is measured while the source voltage $V_s$ and the fluidic-gate voltage $V_{fg}$ are about 0 volts and the drain voltage $V_d$ is greater than zero volts. Further, the sensing layer 124 (see, e.g., FIG. 1) is sensitive to a pH of the fluid 132, whereby a surface potential difference at the sensing layer 124 changes based on the pH. For example, the sensing layer 124 may be hafnium oxide or some other suitable material.

As seen, a first curve 1002 corresponding to a first pH of the fluid 132 and a second curve 1004 corresponding to a second pH of the fluid 132 are substantially the same. Hence, drain current $I_d$ is independent of a pH of the fluid 132. As with FIG. 6, the drain current $I_d$ is independent of pH, despite the sensing layer 124 (see, e.g., FIG. 1) being sensitive to pH, because the pH of the fluid 132 induces the same surface potential shift at the ISFET 102 as at the VRFET 104. Accordingly, the sensor has high sensitivity and high accuracy.

While embodiments of the sensor in FIGS. 3, 4, 7, and 9 illustrate the ISFET 102 and the VRFET 104 as being N-type FETs, the ISFET 102 and the VRFET 104 may be P-type FETs in alternative embodiments. Further, while the ISFET 102 and the VRFET 104 in FIGS. 3, 4, 7, and 9 are described as corresponding to embodiments in FIG. 1, the ISFET 102 and the VRFET 104 may correspond to embodiments in any one or combination of FIGS. 2A-2F.

Figure 11:
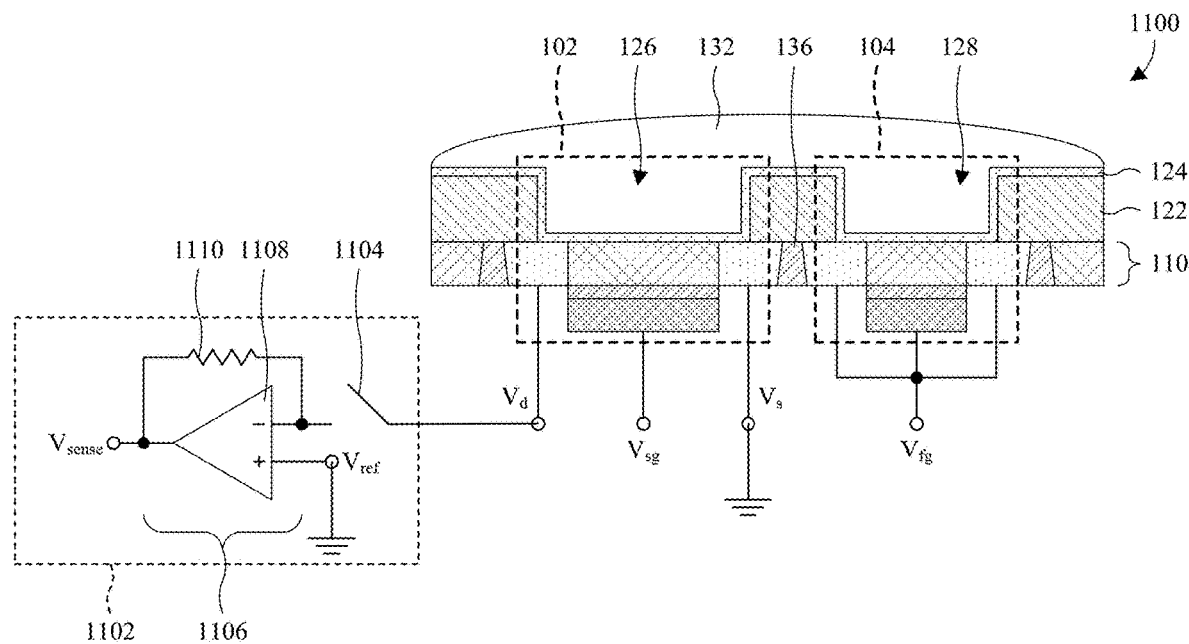
FIG. 11 illustrates a cross-sectional view of some embodiments of the sensor of FIG. 1 in which the ISFET is electrically coupled to a sensing circuit.

With reference to FIG. 11, a cross-sectional view 1100 of some embodiments of the sensor of FIG. 1 is provided in which the ISFET 102 is electrically coupled to a sensing circuit 1102. The sensing circuit 1102 generates a sense voltage $V_{sense}$ proportional to the drain current flowing from a drain of the ISFET 102 to a source of the ISFET 102 and may, for example, be used with the transient/RTS/pulse/noise readout methodology of FIG. 9. Further, the sensing circuit 1102 comprises a sampling switch 1104 and a current-to-voltage converter 1106.

The sampling switch 1104 is electrically coupled to a drain of the ISFET 102 and the current-to-voltage converter 1106 is selectively electrically coupled to the drain of the ISFET 102 by the sampling switch 1104. The source of the ISFET 102 is electrically coupled to ground so the source voltage $V_s$ is about 0 volts. The current-to-voltage converter 1106 is configured to convert drain current of the ISFET 102 to a sense voltage $V_{sense}$ and may, for example, be a transimpedance amplifier. In some embodiments, the current-to-voltage converter 1106 comprises an operational amplifier 1108 and a feedback resistor 1110. The feedback resistor 1110 extends from a negative input of the operational amplifier 1108 to an output of the operational amplifier 1108, and the sampling switch 1104 selectively electrically couples the negative input to the drain of the ISFET 102. Further, a positive input of the operational amplifier 1108 is electrically coupled to ground so a reference voltage $V_{ref}$ at the positive input is about 0 volts.

Figure 12:
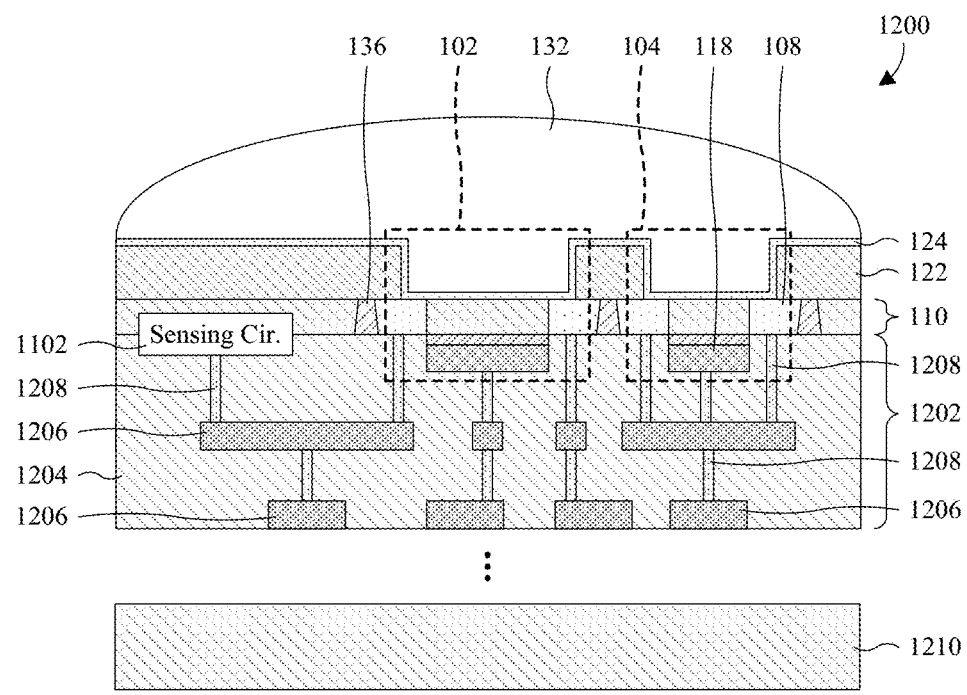
FIG. 12 illustrates a cross-sectional view of some embodiments of the sensor of FIG. 11 in which an interconnect structure underlies and is electrically coupled to the ISFET and the VRFET.

With reference to FIG. 12, a cross-sectional view 1200 of some embodiments of the sensor of FIG. 11 is provided in which the sensing circuit 1102 is on the substrate 110. Further, the ISFET 102 and the VRFET 104 are electrically coupled to an interconnect structure 1202 underlying the substrate 110. The interconnect structure 1202 comprises an interconnect dielectric layer 1204, and further comprises a plurality of wires 1206 and a plurality of vias 1208. The interconnect dielectric layer 1204 may be or comprise, for example, silicon oxide, a low k dielectric, some other suitable dielectric(s), or any combination of the foregoing.

The wires 1206 and the vias 1208 are stacked in the interconnect dielectric layer 1204 and define conductive paths. For example, the wires 1206 and the vias 1208 may define a conductive path electrically coupling the VRFET source/drain regions 108 to the solid VRFET gate electrode 118. As another example, the wires 1206 and the vias 1208 may define a conductive path electrically coupling the ISFET 102 to the sensing circuit 1102. The wires 1206 and the vias 1208 may be or comprise, for example, copper, aluminum copper, tungsten, some other suitable metal(s) and/or conductive material(s), or any combination of the foregoing.

In some embodiments, a carrier substrate 1210 underlies and is bonded to the interconnect structure 1202. The carrier substrate 1210 may be or comprise, for example, a bulk silicon substrate and/or some other suitable substrate.

While the interconnect structure 1202 and the carrier substrate 1210 are shown with regards to embodiments of the sensor in FIG. 11, the interconnect structure 1202 and/or the carrier substrate 1210 may be integrated with the sensor in any one or combination of FIGS. 1, 2A-2F, 3, 4, 7, and 9. For example, the interconnect structure 1202 may electrically couple the ISFET source/drain regions 106 and the solid ISFET gate electrode 116 together, as done for the VRFET source/drain regions 108 and the solid VRFET gate electrode 118, when the interconnect structure 1202 is integrated with embodiments of the sensor in FIG. 4 and/or FIG. 7. While the sensing circuit 1102 is shown with regards to embodiments of the sensor in FIGS. 11 and 12, the sensing circuit 1102 may be integrated with the sensor in any one or combination of FIGS. 1, 2A-2F, 3, 4, 7, and 9.

Figure 13:
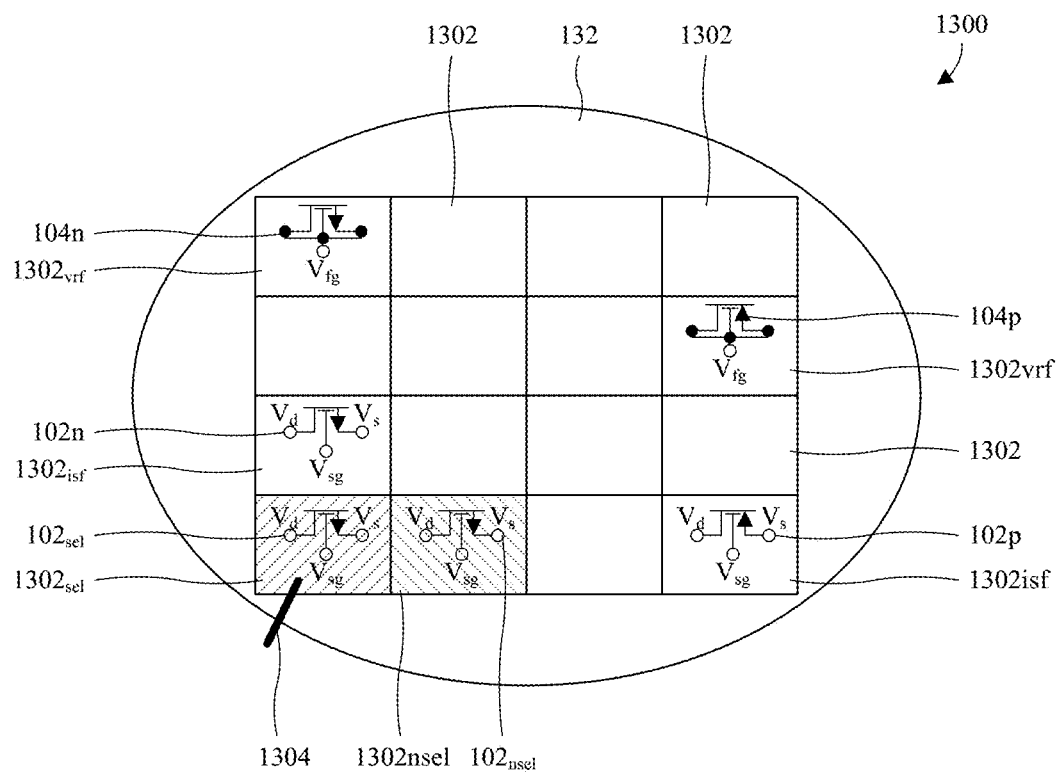
FIG. 13 illustrates a top layout of some embodiments of an array-type sensor comprising an N-type ISFET and a P-type ISFET respectively paired with an N-type VRFET and a P-type VRFET.

With reference to FIG. 13, a top layout 1300 of some embodiments of an array-type sensor is provided. The array-type sensor comprises a plurality of cells 1302 in a plurality of rows and a plurality of columns. The plurality of cells 1302 comprises a plurality of ISFET cells 1302*isf* and a plurality of VRFET cells 1302*vrf*. An N-type ISFET 102*n* and a P-type ISFET 102*p* are respectively at the ISFET cells 1302*isf*. An N-type VRFET 104*n* and a P-type VRFET 104*p* are respectively at the VRFET cells 1302*vrf*.

The N-type VRFET 104*n* serves as a reference electrode for the N-type ISFET 102*n*, and the P-type VRFET 104*p* serves as a reference electrode for the P-type ISFET 102*p*. The N-type ISFET 102*n* and the N-type VRFET 104*n* are more sensitive to targets with a positive polarity than the P-type ISFET 102*p* and the P-type VRFET 104*p*. Similarly, the P-type ISFET 102*p* and the P-type VRFET 104*p* are more sensitive to targets with a negative polarity than the N-type ISFET 102*n* and the N-type VRFET 104*n*. The N-type ISFET 102*n* and the N-type VRFET 104*n* are each separated from the P-type ISFET 102*p* by at least one of the cells 1302 and are each separated from the P-type VRFET 104*p* by at least one of the cells 1302. Without such separation, the N-type ISFET 102*n* and the N-type VRFET 104*n* may interfere with operation the P-type ISFET 102*p* and the P-type VRFET 104*p* and vice versa.

By including the P-type ISFET 102*p* and the P-type VRFET 104*p* together with the N-type ISFET 102*n* and the N-type VRFET 104*n*, the array-type sensor can adapt to and optimally sense targets of different polarities. Targets with a positive polarity may be sensed by the N-type ISFET 102*n* and the N-type VRFET 104*n*, whereas targets with a negative polarity may be sensed by the P-type ISFET 102*p* and the P-type VRFET 104*p*. Hence, the array-type sensor has high sensitivity and high accuracy for targets of different polarities.

In some embodiments, the N-type ISFET 102*n* and the N-type VRFET 104*n* are respectively as the ISFET 102 and the VRFET 104 are illustrated and/or described in any one or combination of FIGS. 1, 2A-2F, 3, 4, 7, 9, 11, and 12. In such embodiments, the ISFET source/drain regions 106 and the VRFET source/drain regions 108 are n-type. Similarly, in some embodiments, the P-type ISFET 102*p* and the P-type VRFET 104*p* are respectively as the ISFET 102 and the VRFET 104 are illustrated and/or described in any one or combination of FIGS. 1, 2A-2F, 3, 4, 7, 9, 11, and 12. In such embodiments, the ISFET source/drain regions 106 and the VRFET source/drain regions 108 are p-type.

In some embodiments, the plurality of cells 1302 comprises a selective cell 1302sel at which a selective ISFET 102sel is located, and further comprises a non-selective cell 1302nsel at which a non-selective ISFET 102nsel is located. The selective ISFET 102sel includes a plurality of sensing probes that selectively bind with or otherwise react with a target to change a surface potential difference at a sensing surface of the selective ISFET 102sel. The non-selective ISFET 102nsel includes a plurality of sensing probes that do not selectively bind with or otherwise react with the target. For example, the sensing probes of the non-selective ISFET 102nsel may be selective towards a different target. In alternative embodiments, the non-selective ISFET 102nsel excludes sensing probes. The selective and non-selective ISFETs 102sel, 102nsel may, for example, be employed for differential sensing of the target and other suitable sensing approaches. The selective ISFET 102sel and the non-selective ISFET 102nsel may, for example, be N-type (as illustrated) when the target has a positive polarity and may, for example, be P-type when the target has a negative polarity for high sensitivity.

In some embodiments, the selective ISFET 102sel and/or the non-selective ISFET 102nsel is/are as the ISFET 102 of FIG. 2D is illustrated and/or described. In alternative embodiments, the selective ISFET 102sel and/or the non-selective ISFET 102nsel is/are as the ISFET 102 in any one FIGS. 1, 2A-C, 2E, 2F, 3, 4, 7, 9, 11, and 12 is illustrated and/or described with the addition of the sensing probes 202 in FIG. 2D. In embodiments in which the selective ISFET 102sel and the non-selective ISFET 102nsel both have sensing probes, the sensing probes are selective to different targets.

In some embodiments, the plurality of cells 1302 further comprises a cell at which a reference electrode 1304 is located. In contrast with a VRFET, the reference electrode 1304 is not integrated with the ISFETs on a common substrate. The reference electrode 1304 may, for example, be an Ag/AgCl reference electrode or some other suitable reference electrode. The reference electrode 1304 may, for example, be used to bias the fluid 132 for the N-type ISFET 102n, the P-type ISFET 102p, the selective ISFET 102sel, the non-selective ISFET 102nsel, any other ISFET in the array-type sensor, or any combination of the foregoing.

Figure 14A:
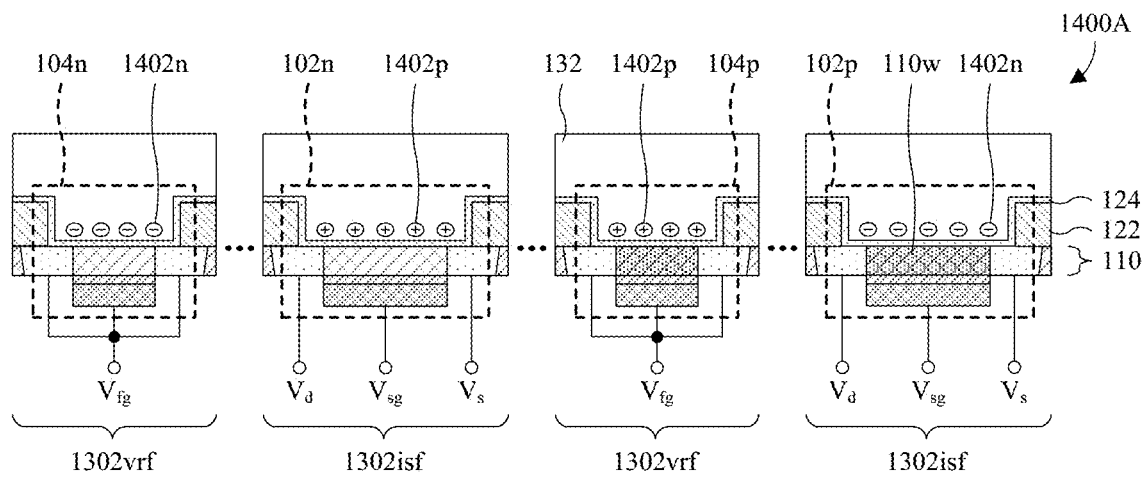
FIGS. 14A-14C illustrate cross-sectional views of some embodiments of the array-type sensor of FIG. 13.

With reference to FIG. 14A, a cross-sectional view 1400A of some embodiments of the array-type sensor of FIG. 12 is provided in which the array-type sensor comprises the N-type ISFET 102n, the N-type VRFET 104n, the P-type ISFET 102p, and the P-type VRFET 104p on a common substrate 110. In some embodiments (as illustrated), the N-type ISFET 102n and the N-type VRFET 104n are on a bulk region of the substrate 110, whereas the P-type ISFET 102p and the P-type VRFET 104p are on a well region 110w of the substrate. Hence, the well region 110w is N-type, whereas the bulk of the substrate 110 is P-type. In alternative embodiments, the N-type ISFET 102n and the N-type VRFET 104n are on the well region 110w, whereas the P-type ISFET 102p and the P-type VRFET 104p are on the bulk of the substrate 110.

In some embodiments, the N-type VRFET 104n is used to bias the fluid 132 for the N-type ISFET 102n and/or the P-type VRFET 104p is used to bias the fluid 132 for the P-type ISFET 102p. In alternative embodiments, the reference electrode 1304 of FIG. 13 (not shown) is used to bias the fluid 132 for the N-type ISFET 102n and/or the P-type ISFET 102p. In some embodiments, positive charge 1402p accumulates on sensing surfaces respectively of the N-type ISFET 102n and the P-type VRFET 104p, whereas negative charge accumulates on sensing surfaces respectively of the P-type ISFET 102p and the N-type VRFET 104n, during use of the array-type sensor.

Figure 14B:
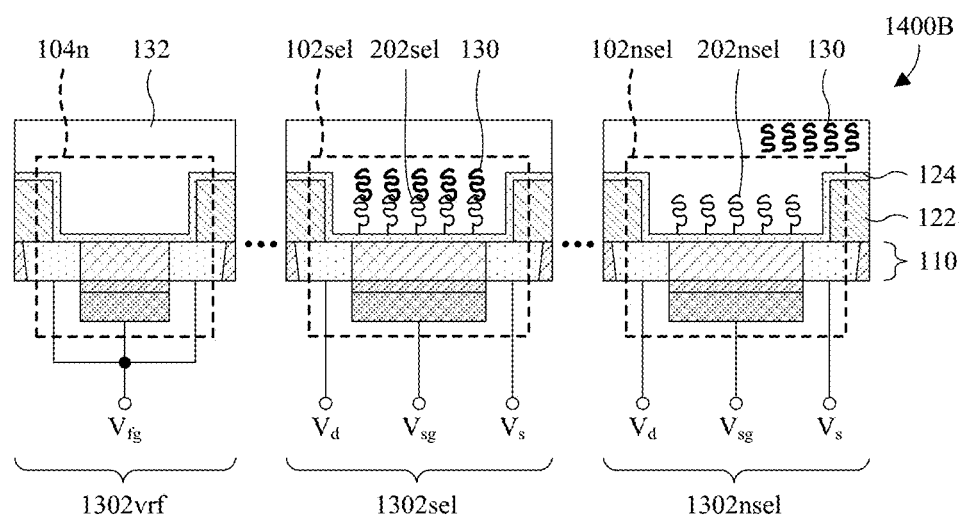

With reference to FIG. 14B, a cross-sectional view 1400B of some embodiments of the array-type sensor of FIG. 13 is provided in which the array-type sensor comprises the selective ISFET 102sel and the non-selective ISFET 102nsel. The selective ISFET 102sel comprises a plurality of sensing probes 202sel that selectively bind to a target 130. The non-selective ISFET 102nsel comprises a plurality of sensing probes 202nsel that do not selectively bind to the target 130. In some embodiments (as illustrated), the target 130, the selective sensing probes 202sel, and the non-selective sensing probes 202nsel are nucleic acids. Further, in at least some of such embodiments, the selective sensing probes 202sel are complementary to the target 130, whereas the non-selective sensing probes 202nsel are not complementary to the target 130. In alternative embodiments, other types of targets and sensing probes are used.

In some embodiments (as illustrated), the selective ISFET 102sel and the non-selective ISFET 102nsel are N-type, whereby the N-type VRFET 104n is used to bias the fluid 132 for the selective ISFET 102sel and/or the non-selective ISFET 102nsel. In alternative embodiments, the selective ISFET 102sel and the non-selective ISFET 102nsel are P-type, whereby the P-type VRFET 104p of FIG. 13 (not shown) is used to bias the fluid 132 for the selective ISFET 102sel and/or the non-selective ISFET 102nsel. In alternative embodiments, the reference electrode 1304 of FIG. 13 (not shown) is used to bias the fluid 132 for the selective ISFET 102sel and/or the non-selective ISFET 102nsel.

Figure 14C:
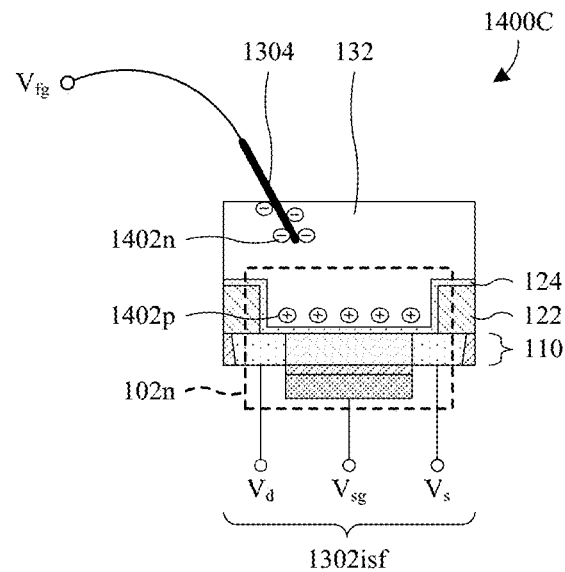

With reference to FIG. 14C, a cross-sectional view 1400C of some embodiments of the array-type sensor of FIG. 13 is provided in which the array-type sensor comprises the N-type ISFET 102n and the reference electrode 1304. In some embodiments (as illustrated), the reference electrode 1304 is used to bias the fluid for the N-type ISFET 102n. In alternative embodiments, the N-type VRFET 104n of FIG. 13 (not shown) is used to bias the fluid 132 for the N-type ISFET 102n. In some embodiments, positive charge 1402p accumulates on a sensing surface of the N-type ISFET 102n, whereas negative charge 1402n accumulates on the reference electrode 1304, during use. In alternative embodiments of the array-type sensor, the P-type ISFET 102p, the selective ISFET 102sel, the non-selective ISFET 102nsel, or any combination of the foregoing is/are used in place of the N-type ISFET 102n.

Figure 15:
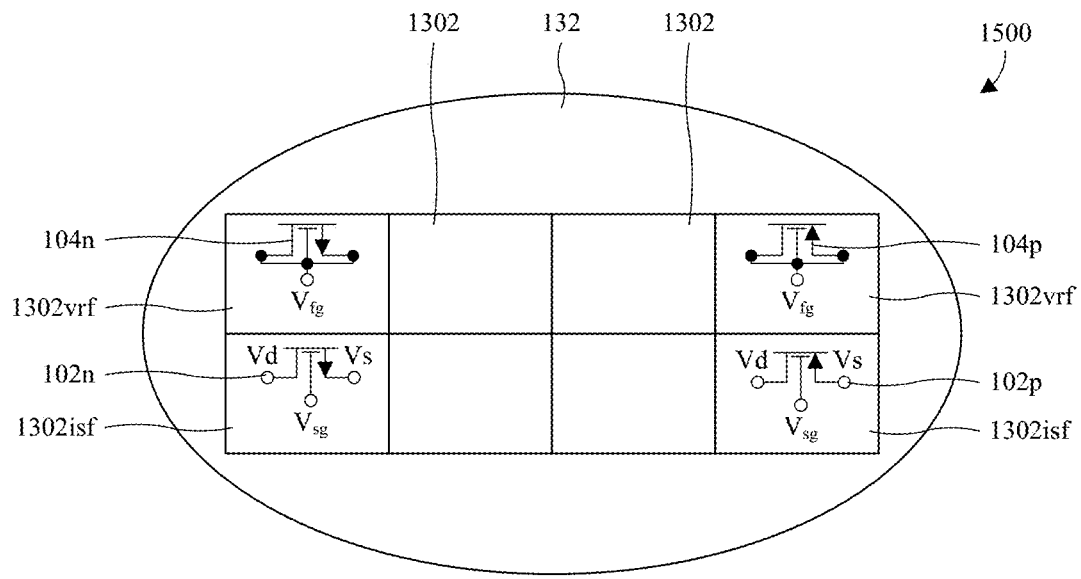
FIG. 15 illustrates a top layout of some alternative embodiments of the array-type sensor of FIG. 13 having a different number of rows.

With reference to FIG. 15, a top layout 1500 of some alternative embodiments of the array-type sensor of FIG. 13 is provided in which the array-type sensor has a different number of rows. Further, the selective and non-selective ISFETs 102sel, 102nsel and the reference electrode 1304 are omitted.

Figure 16:
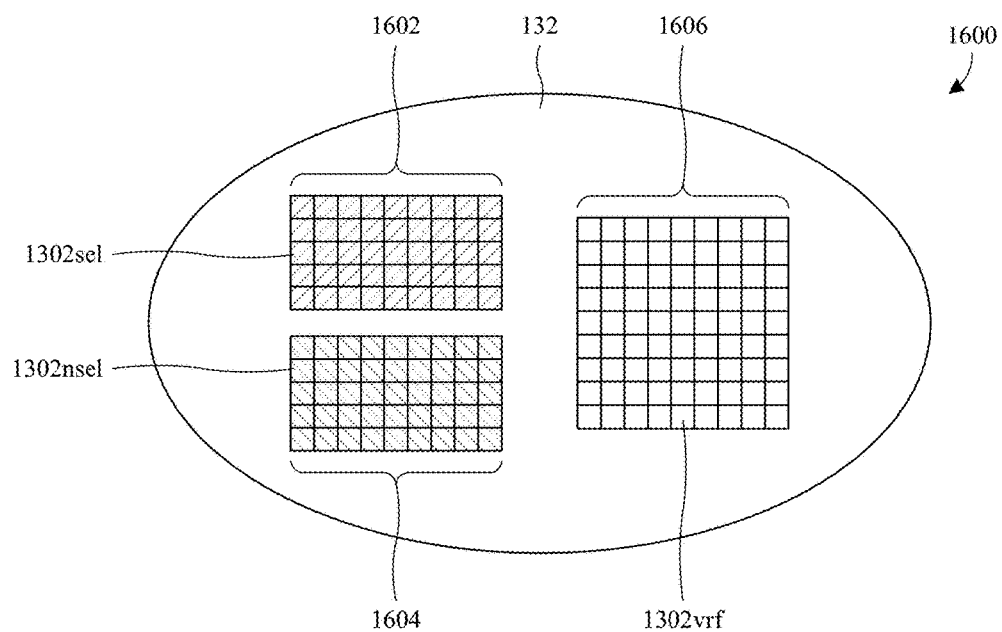
FIG. 16 illustrates a top layout of some embodiments of an array-type for deoxyribonucleic acid (DNA) hybridization.

With reference to FIG. 16, a top layout 1600 of some embodiments of an array-type sensor for deoxyribonucleic acid (DNA) hybridization is provided. A selective sensor array 1602 comprises a plurality of selective cells 1302sel in a plurality of rows and a plurality of columns. Similarly, a non-selective sensor array 1604 comprises a plurality of non-selective cells 1302nsel in a plurality of rows and a plurality of columns. The selective cells 1302sel comprise individual selective ISFETs that selectively bind to a target, whereas the non-selective cells comprise individual non-selective ISFETs that do not bind to the target. The selective and non-selective cells 1302sel, 1302nsel may, for example, be as described with regard to FIG. 13 and/or may, for example, be as illustrated in FIG. 14B.

In some embodiments, the selective sensor array 1602 and the non-selective sensor array 1604 have the same size, such that there is a one-to-one correspondence between the selective cells 1302sel and the non-selective cells 1302nsel. This may, for example, allow differential sensing of multiple samples simultaneously. For example, each sample may be added to an individual selective cell and an individual non-selective cell corresponding to the individual selective cell for differential sensing.

A VRFET electrode array 1606 comprises a plurality of VRFET cells 1302vrf in a plurality of rows and a plurality of columns. The VRFET cells 1302vrf comprise individual VRFETs. The VRFET cells 1302vrf may, for example, be as described with regard to FIG. 13 and/or may, for example, be as illustrated in FIGS. 14A and 14B. In some embodiments, the VRFET cells 1302vrf are used in tandem to bias the fluid 132 around the selective sensor array 1602 and the non-selective sensor array 1604. In alternative embodiments, only one or a subset of the VRFET cells 1302vrf are used at any given time.

Figure 17A:
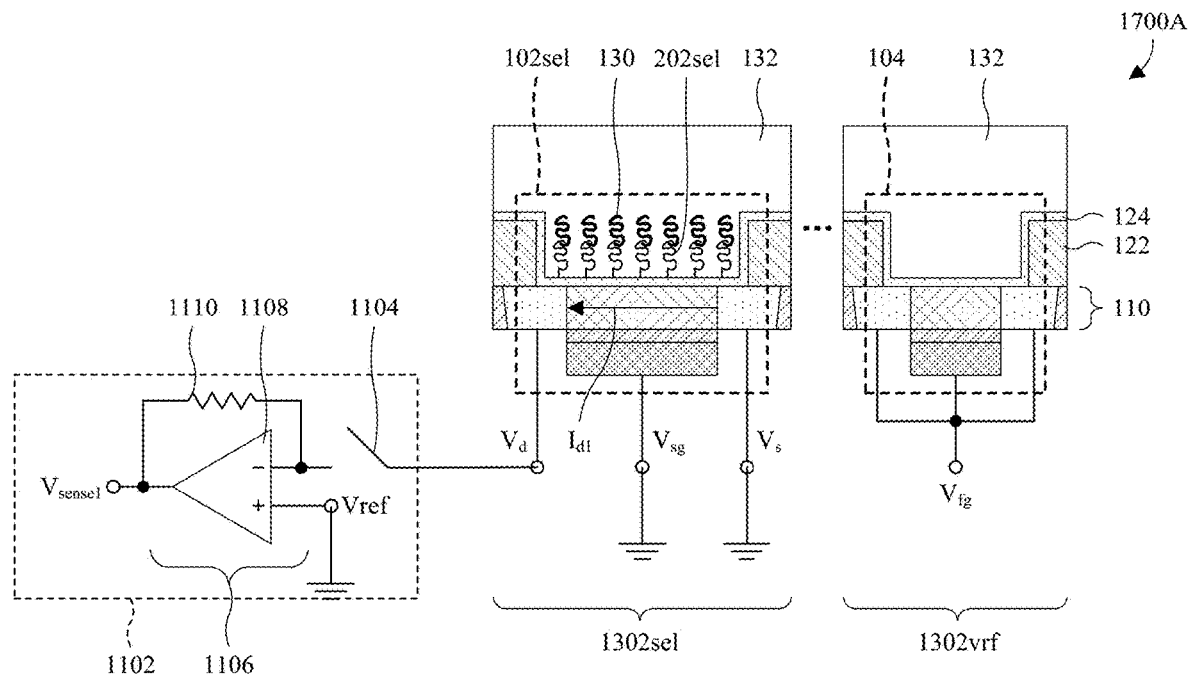
FIGS. 17A and 17B illustrate cross-sectional views of selective and non-selective cells in the array-type sensor of FIG. 16 during sensing.
Figure 17B:
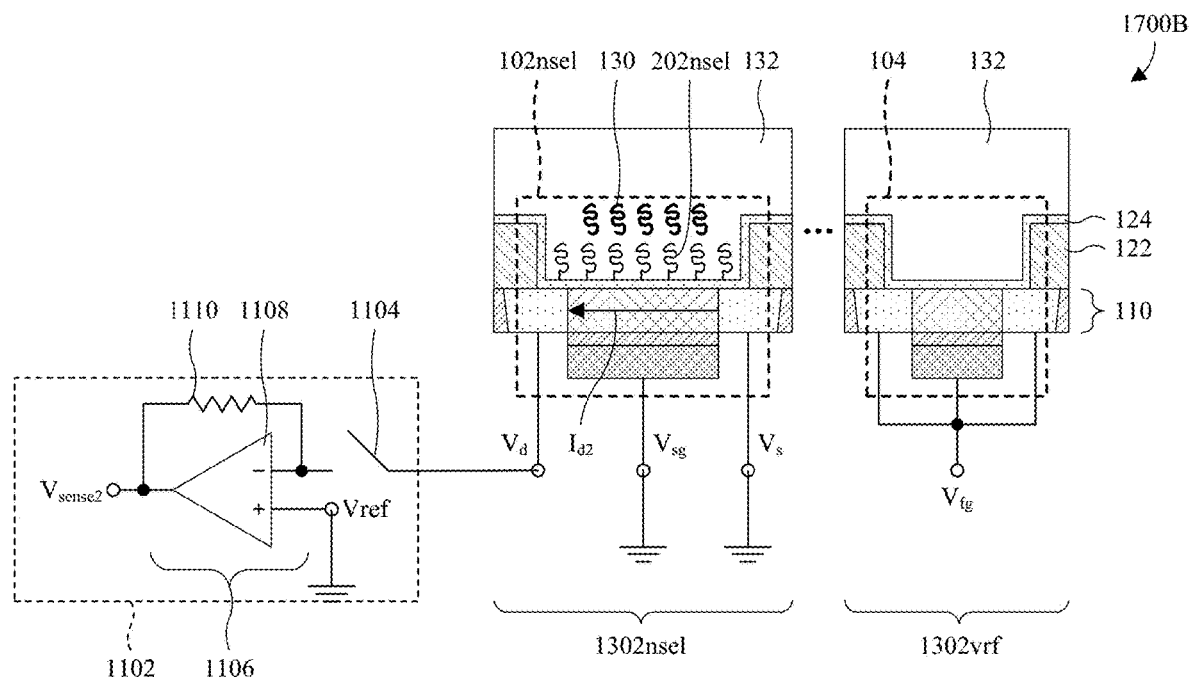

With reference to FIGS. 17A and 17B, cross-sectional views 1700A, 1700B of some embodiments of a selective cell 1302sel of FIG. 16 and a non-selective cell 1302nsel of FIG. 16 during sensing is provided. The fluid 132 is biased with a fluidic-gate voltage $V_{fg}$ using a VRFET 104 at a VRFET cell 1302vrf (shown in both FIGS. 17A and 17B). The biasing induces a first drain current $I_{d1}$ to flow at the selective cell 1302sel (see FIG. 17A) and further induces a second drain current $I_{d2}$ to flow at the non-selective cell 1302nsel (see FIG. 17B). Further, a target 130 is added to both the selective cell 1302sel and the non-selective cell 1302nsel.

The target 130 binds to a plurality of sensing probes 202sel at the selective cell 1302sel (see FIG. 17A) since the sensing probes 202sel at the selective cell 1302sel are selective of the target 130. The binding changes a surface potential difference at the selective cell 1302sel, which changes the first drain current $I_{d1}$. However, the target 130 does not bind to a plurality of sensing probes 202nsel at the non-selective cell 1302nsel (see FIG. 17B) since the sensing probes 202nsel at the non-selective cell 1302nsel are not selective to the target 130. Hence, the second drain current $I_{d2}$ is unaffected or minimally affected by the target 130. The target 130 and the selective sensing probes 202sel may, for example, be or comprise complementary nucleic acids that strongly bind together. The target 130 and the non-selective sensing probes 202nsel may, for example, be or comprise nucleic acids that are not complementary and hence do not or weakly bind together.

In some embodiments, the selective cell 1302sel and the non-selective cell 1302nsel have individual sensing circuits 1102. The sensing circuits 1102 convert the first drain current $I_{d1}$ and the second drain current $I_{d2}$ respectively to a first sense voltage $V_{sense1}$ and a second sense voltage $V_{sense2}$. The sensing circuits 1102 may, for example, each be as their counterpart is illustrated and/or described with regard to FIG. 11.

Figure 18A:
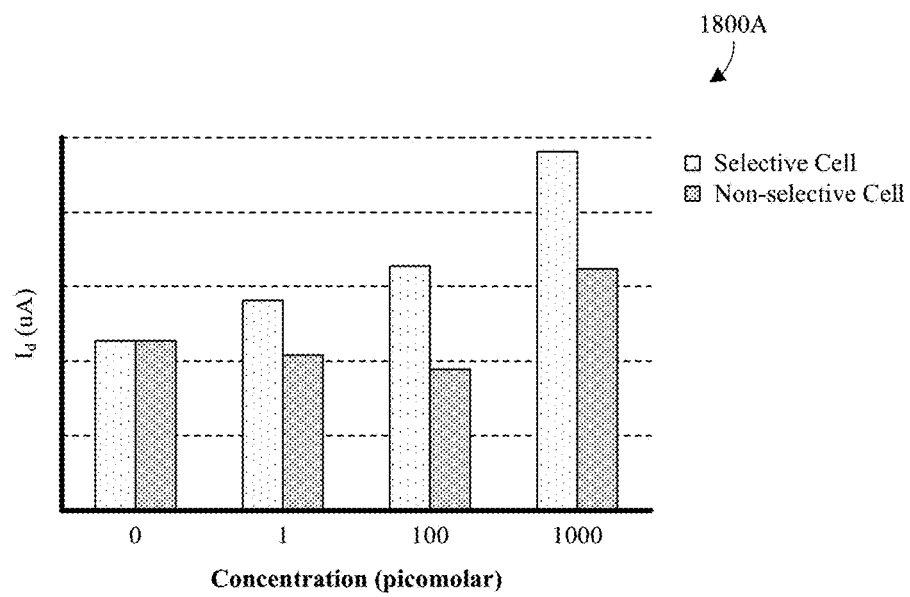
FIGS. 18A-18C illustrate graphs of some embodiments of sensing results during the sensing of FIGS. 17A and 17B.

With reference to FIG. 18A, a graph 1800A of some embodiments of differential sensing results during the sensing of FIGS. 17A and 17B is provided. The lateral axis of the graph 1800A is logarithm and corresponds to target concentration, whereas the vertical axis of the graph 1800A is linear and corresponds to drain current. Drain current is measured at the selective and non-selective cells 1302sel, 1302nsel for different concentrations of the target. These different concentrations include 0 picomolars (pM), 1 pM, 100 pM, and 1000 pM. As seen, the drain currents (i.e., the first and second drain currents $I_{d1}$, $I_{d2}$) are different between the selective and non-selective cells 1302sel, 1302nsel, except where the target concentration is zero. Hence, differential sensing may be used to identify different target concentrations.

Figure 18B:
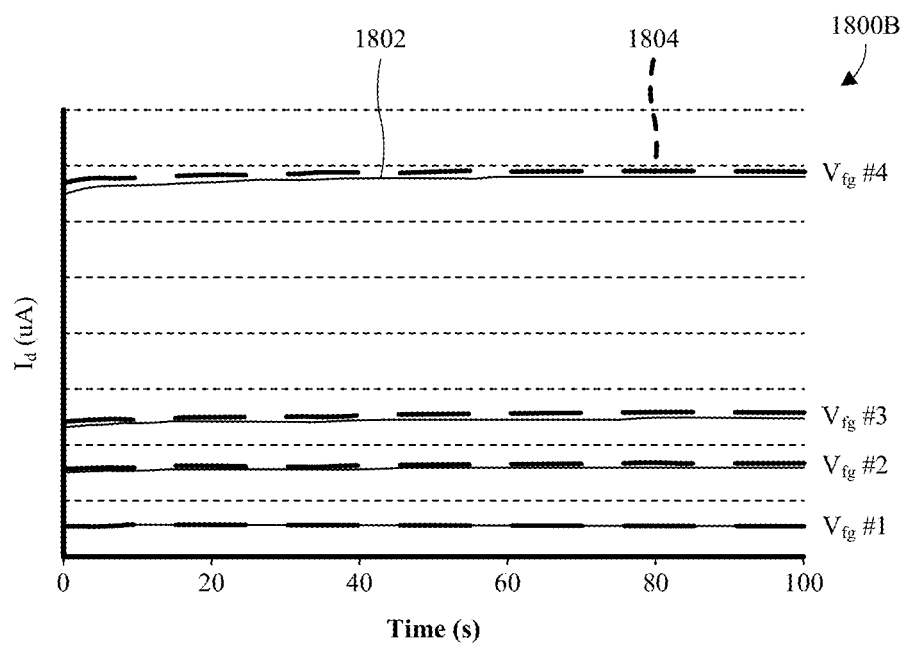

With reference to FIG. 18B, a graph 1800B of some embodiments of sensing results over time during the sensing of FIGS. 17A and 17B is provided. The lateral axis of the graph 1800B corresponds to time, whereas the vertical axis of the graph 1800B corresponds to the first drain current $I_{d1}$ of the selective cell 1302sel (see FIG. 17A). Drain current is measured for multiple different pHs and for multiple different fluidic-gate voltages $V_{fg}$. A plurality of first-pH curves 1802 corresponds to a first pH of the fluid 132 (see FIG. 17A) and is schematically illustrated by solid black curves. A plurality of second-pH curves 1804 corresponds to a second pH of the fluid 132 and is schematically illustrated by dashed curves.

As seen, the first-pH curves 1802 and the second-pH curve 1804 are substantially the same. Hence, drain current is independent of, or substantially independent of, pH. Drain current may be independent of pH because the pH of the fluid 132 induces the same surface potential shift at the selective ISFET 102sel (see FIG. 17A) as at the VRFET 104 (see FIG. 17A), whereby the effect of pH is cancelled. Also seen, drain current is quick to reach steady state. For example, it may take only a few seconds to level off. This allows high sensing throughput.

Figure 18C:
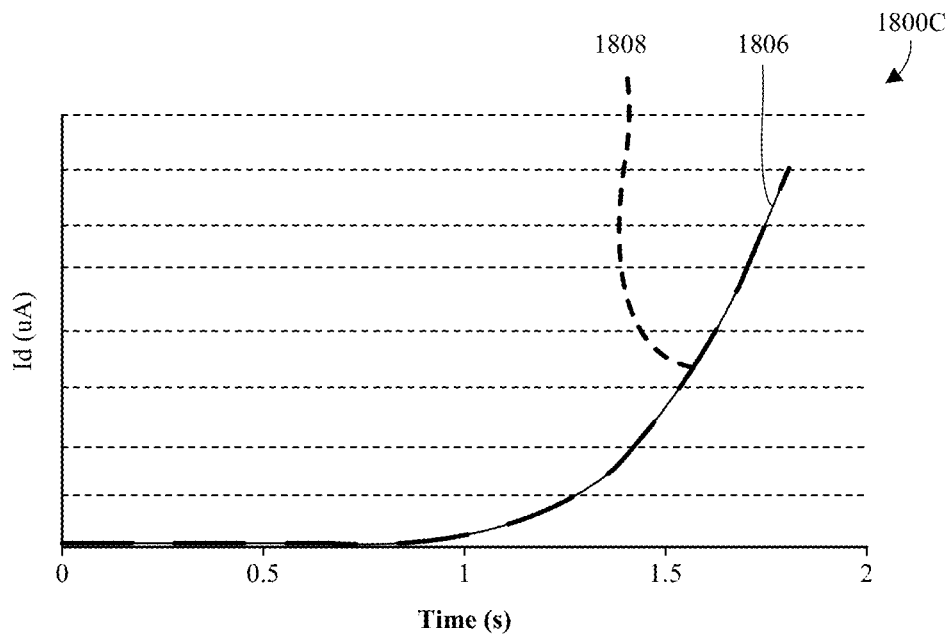

With reference to FIG. 18C, a graph 1800C of some embodiments of sensing results over time during the sensing of FIGS. 17A and 17B is provided in which the sensing results are collected multiple times. The lateral axis of the graph 1800C corresponds to time, whereas the vertical axis of the graph 1800C corresponds to the first drain current $I_{d1}$ of the selective cell 1302sel (see FIG. 17A). A first curve 1806 corresponds to sensing results collected first, and a second curve 1808 corresponds to sensing results collected second. As seen, the first and second curves 1806, 1808 are substantially the same. Hence, sensing results are stable and drift is low.

While FIGS. 13 and 15 show the array-type sensor with specific numbers of rows and columns, the array-type sensor may have other numbers of rows and columns. For example, the array-type sensor may more generally have m rows and n columns, where m and n are integer variables and m+n is greater than or equal to 5. Similarly, while FIG. 16 shows the selective sensor array 1602, the non-selective sensor array 1604, and the VRFET electrode array 1606 with specific numbers of rows and columns, different numbers of rows and columns are amenable. While the array-type sensor of FIG. 16 employs the VRFET electrode array 1606 for biasing the fluid 132, other types of reference electrode arrays may be used in alternative embodiments. For example, an Ag/AgCl reference electrode array or some other suitable type of reference electrode array may alternatively be used.

Figure 19A:
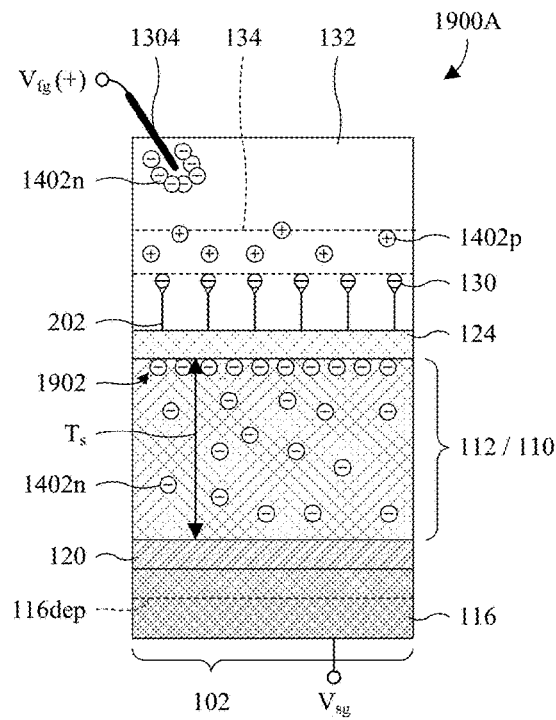
FIGS. 19A and 19B illustrate cross-sectional views of some embodiments of a sensor comprising an ISFET in which a body region of the ISFET is fully depleted and/or is lightly doped or undoped.

With reference to FIG. 19A, a cross-sectional view 1900A of some embodiments of a sensor comprising an ISFET 102 is provided in which the ISFET 102 is n-type and the ISFET body region 112 of the ISFET 102 is fully depleted and/or is lightly doped or undoped. As such, parasitic elements between a reference electrode 1304 and the solid ISFET gate electrode 116 are reduced. For example, parasitic capacitances and resistances from the ISFET body region 112 and/or from the ISFET source/drain regions (not shown) is/are reduced. By reducing the parasitic elements, a channel 1902 in the ISFET body region 112 is mainly affected by the fluid 132, not parasitic elements. Hence, the sensor may have high sensitivity and high accuracy.

In some embodiment, full depletion is achieved by: 1) limiting the ISFET body region 112 to a small thickness $T_s$; and/or 2) lightly doping the ISFET body region 112 or otherwise leaving the ISFET body region 112 undoped. The thickness $T_s$ may, for example, be about 10-25 nanometers, less than about 25 nanometers, less than about 10 nanometers, or some other suitable value. The light doping may, for example, be less than about $5 \times 10^{15}$ cm$^{-3}$ or some other suitable value.

During use of the ISFET 102, a reference electrode 1304 is biased with a positive fluidic-gate voltage $V_{fg}$ to induce formation of the channel 1902 from mobile electrons. The channel 1902 extends laterally from a drain region (not shown) of the ISFET 102 to a source region (not shown) of the ISFET 102. See, for example, the ISFET source/drain regions 106 in FIG. 1. Further, the sensing layer 124 and a plurality of sensing probes 202 react with and/or bind to a target 130 with a negative polarity. This results in variations to an impedance of the channel 1902 and hence allows the target 130 to be characterized and/or identified. The target 130 and the sensing probes 202 may, for example, respectively be antigens and antibodies. However, other types of targets and/or other types of sensing probes 202 are amenable.

In some embodiments, the reference electrode 1304 is an Ag/AgCl reference electrode or some other suitable reference electrode. In some embodiments, the solid ISFET gate electrode 116 has a gate depletion region 116*dep* due to a PN junction between the solid ISFET gate electrode 116 and the ISFET body region 112. For example, where the ISFET body region 112 is lightly doped with P-type dopants and the solid ISFET gate electrode 116 is polysilicon doped with N-type dopants, the gate depletion region 116*dep* may form.

Figure 19B:
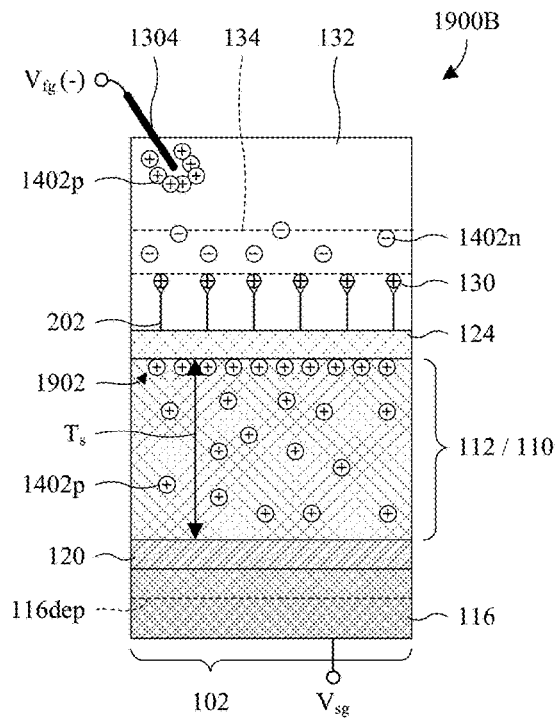

With reference to FIG. 19B, a cross-sectional view 1900B of some alternative embodiments of the sensor of FIG. 19A is provided in which the ISFET 102 is p-type. Further, the target 130 has a positive polarity and the reference electrode 1304 is biased with a negative fluidic-gate voltage $V_{fg}$ to induce formation of the channel 1902 from mobile holes. In some embodiments, the ISFET body region 112 is lightly doped with N-type dopants and the solid ISFET gate electrode 116 is polysilicon doped with P-type dopants to form the gate depletion region 116*dep*.

Figure 20:
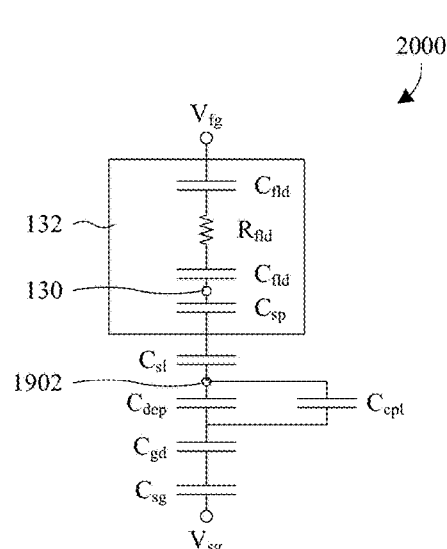
FIG. 20 illustrates a circuit diagram of some embodiments of parasitic elements between the ISFET of FIGS. 19A and 19B and a reference electrode of FIGS. 19A and 19B.

With reference to FIG. 20, a circuit diagram 2000 of some embodiments of parasitic elements between the ISFET 102 of FIGS. 19A and 19B and the reference electrodes 1304 of FIGS. 19A and 19B is provided. A plurality of parasitic capacitors and a parasitic resistor $R_{fld}$ are electrically coupled in series from the reference electrode 1304 (see, e.g., FIG. 19A) to the solid ISFET gate electrode 116 (see, e.g., FIG. 19A). The plurality of capacitors comprises a solid-gate capacitor $C_{sg}$, a gate-dielectric capacitor $C_{gd}$, a depletion-region capacitor $C_{dep}$, a sensing-layer capacitor $C_{sl}$, a sensing-probe capacitor $C_{sp}$, and a pair of fluid capacitors $C_{fld}$. Further, a parasitic coupling capacitor $C_{cpl}$ is in parallel with the depletion-region capacitor $C_{dep}$.

Because the ISFET body region 112 is fully depleted, and/or is lightly doped or undoped, a parasitic resistor from the ISFET body region 112 and parasitic capacitors from the ISFET source/drain regions may, for example, be omitted between the sensing-layer capacitor $C_{sl}$ and the gate-dielectric capacitor $C_{gd}$. Hence, parasitic elements have less effect on the channel 1902 and hence the sensor is more sensitive to the target 130. Note that the channel 1902 and the target 130 are schematically illustrated by circles with different hashing.

Figure 21A:
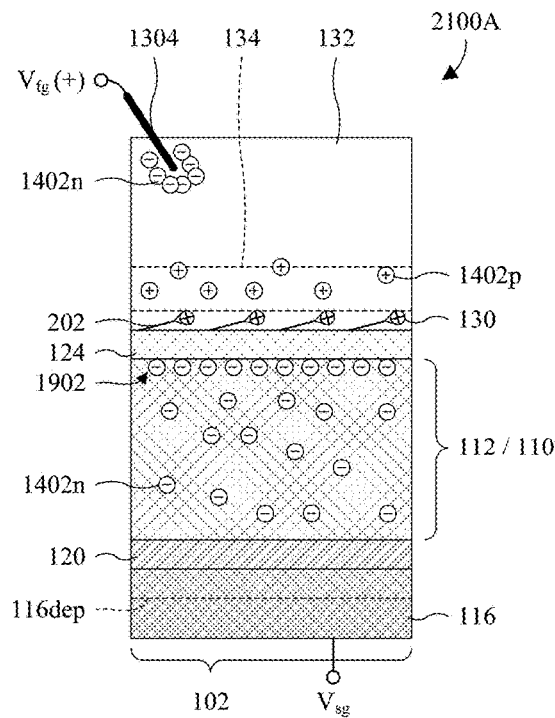
FIGS. 21A and 21B illustrate cross-sectional views of some alternative embodiments of the sensors of FIGS. 19A and 19B in which a target and a reference electrode have the same polarity.
Figure 21B:
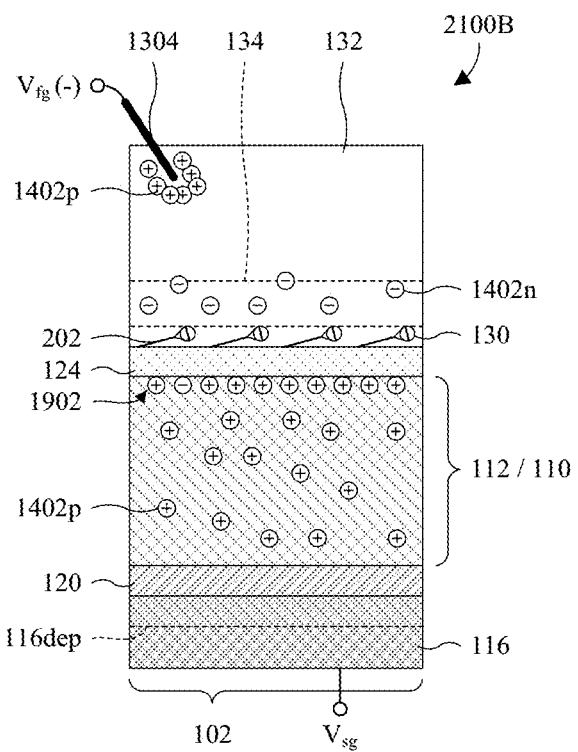

With reference to FIGS. 21A and 21B, cross-sectional views 2100A, 2100B respectively of some alternative embodiments of the sensors of FIGS. 19A and 19B are provided in which the target 130 and the reference electrode 1304 have the same polarity. Because the target 130 and the reference electrode 1304 have the same polarity, the target 130 is electrostatically repelled from the reference electrode 1304 towards the sensing layer 124. As a result, the target 130 is closer to the channel 1902 and the sensing-probe capacitor $C_{sp}$ of FIG. 20 may, for example, be omitted. This, in turn, enhance sensitivity and accuracy.

Figure 22:
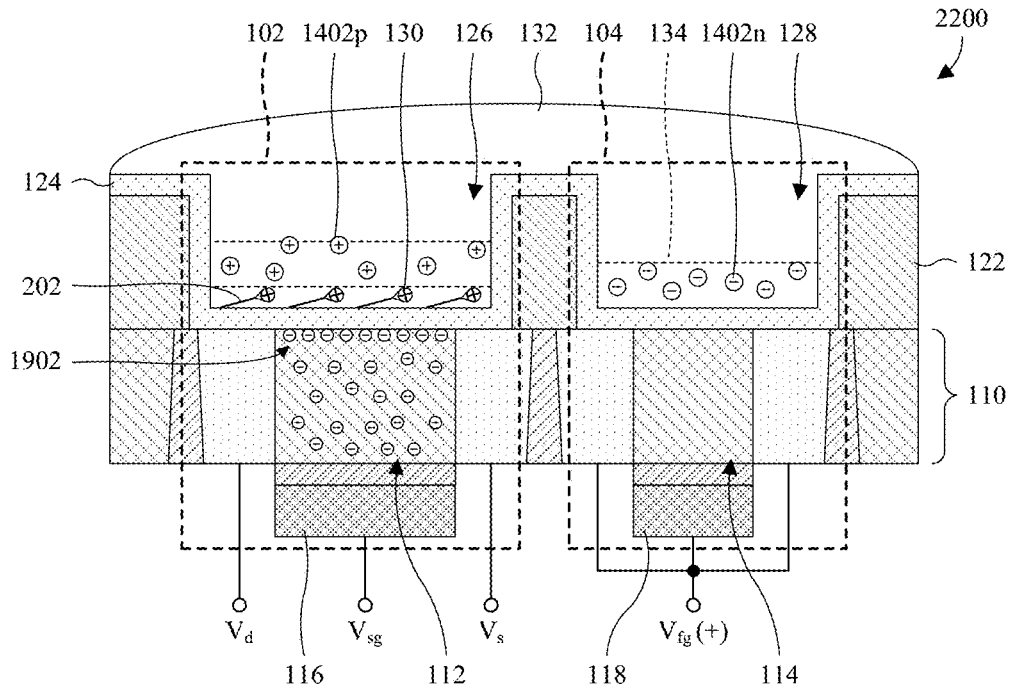
FIG. 22 illustrates a cross-sectional view of some alternative embodiments of the sensor of FIG. 21A in which a VRFET is used in place of the reference electrode.

With reference to FIG. 22, a cross-sectional view 2200 of some alternative embodiments of the sensor of FIG. 21A is provided in which a VRFET is used in place of the reference electrode 1304. The ISFET 102 and the VRFET 104 are N-type and the fluid 132 is biased through the VRFET 104 with a positive fluidic-gate voltage $V_{fg}$ to induce formation of the channel 1902 in the ISFET body region 112. Further, the target 130 has a positive polarity, such that the target 130 is electrostatically repelled from the VRFET 104 towards the sensing layer 124.

While FIG. 22 is illustrated using embodiments of the ISFET 102 in FIG. 21A, embodiments of the ISFET 102 in any one of FIGS. 19A, 19B, and 21B may alternatively be used. In such alternative embodiments, the VRFET 104 is of the same type (N-type or P-type) as the ISFET 102 and the polarities for the fluidic-gate voltage $V_{fg}$ and for the target 130 are as in the corresponding one of FIGS. 19A, 19B, and 21B. While FIG. 22 is illustrated using embodiments of the sensor in FIG. 2D, embodiments of the sensor from any one of FIGS. 1, 2A-2C, 2E, 2F, 11, 12, and 14A-14C may alternatively be used. While not illustrated, the ISFET 102 in any one of FIGS. 19A, 19B, 21A, 21B, and 22 or any one of the alternative embodiments just described may be used in the array-type sensors of FIGS. 13, 15, and 16.

While not discussed, it should be appreciated that readout at the array-type sensors of FIGS. 13, 14A-14C, 15, and 16 and the sensors of FIGS. 19A, 19B, 21A, 21B, and 22 may, for example, be performed using any suitable readout methodology. For example, any one of the AC impedance readout methodology (discussed above), the DC/AC potentiometric readout methodology (discussed above), and the transient/RTS/pulse/noise readout methodology (discussed above) may be used.

With reference to FIGS. 23A-23F, a series of cross-sectional views 2300A-2300F of some embodiments of a method for forming a sensor comprising an ISFET and a VRFET using a semiconductor-on-insulator (SOI) substrate is provided. The method and variations thereof may, for example, be used to form the sensor in any one of the preceding figures.

Figure 23A:
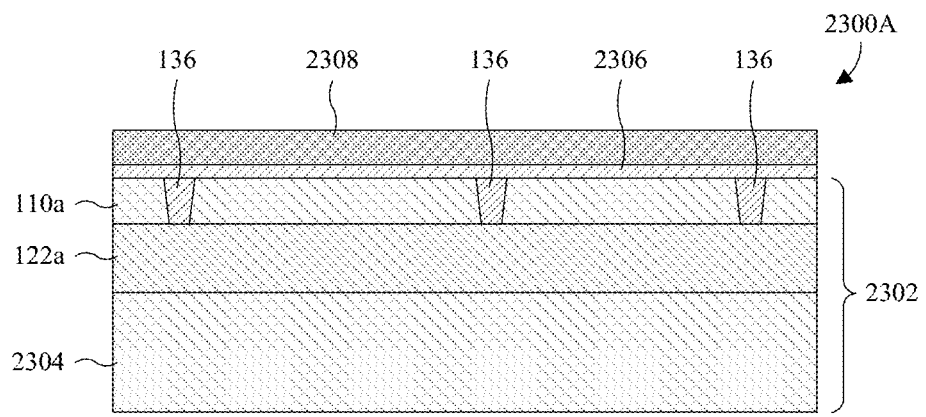
FIGS. 23A-23F illustrate a series of cross-sectional views of some embodiments of a method for forming a sensor comprising an ISFET and a VRFET using a semiconductor-on-insulator (SOI) substrate.

As illustrated by the cross-sectional view 2300A of FIG. 23A, an SOI substrate 2302 is provided. The SOI substrate 2302 comprises a bulk layer 2304 and further comprises a substrate dielectric layer 122*a* and a device layer 110*a* stacked over the bulk layer 2304. As seen hereafter, the bulk layer 2304 is sacrificial. In some embodiments, the device layer 110*a* is lightly doped and/or undoped to reduce parasitic resistances and/or capacitances. See, for example, the discussion with regard to FIG. 19A. The bulk layer 2304 and the device layer 110*a* may, for example, be or comprise silicon and/or some other suitable semiconductor(s), whereas the substrate dielectric layer 122a may be or comprise, for example, silicon oxide and/or some other suitable dielectric(s).

Also illustrated by the cross-sectional view 2300A of FIG. 23A, a trench isolation structure 136 is formed extending into the device layer 110a. Further, a dielectric layer 2306 and a conductive layer 2308 are formed stacked over the trench isolation structure 136 and the device layer 110a. The trench isolation structure 136 may, for example, be formed by patterning the device layer 110a with a photolithography/etching process and subsequently filling resulting trenches with a dielectric material. Other processes are, however, amenable. The dielectric layer 2306 may, for example, be formed by vapor deposition, thermal oxidation, some other suitable deposition process(es), or any combination of the foregoing. The conductive layer 2308 may, for example, be formed by vapor deposition, electroplating, electroless plating, some other suitable deposition process(es), or any combination of the foregoing.

Figure 23B:
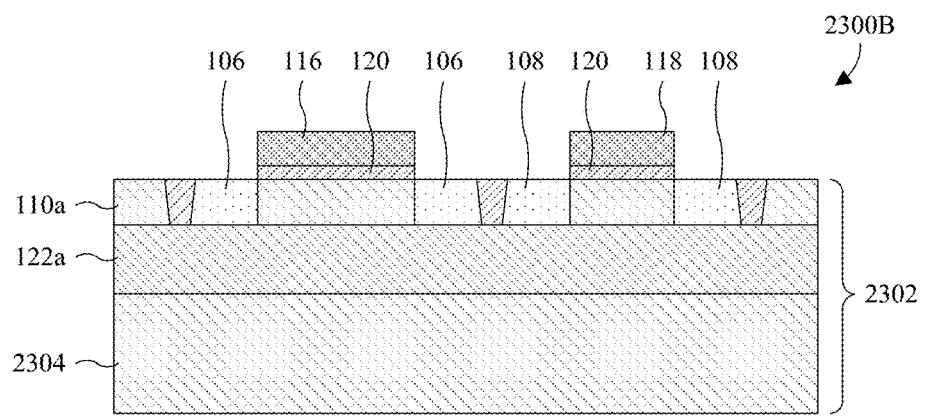

As illustrated by the cross-sectional view 2300B of FIG. 23B, the dielectric layer 2306 (see FIG. 23A) and the conductive layer 2308 (see FIG. 23A) are patterned to form a solid ISFET gate electrode 116 and a solid VRFET gate electrode 118 separated from the device layer 110a by individual gate dielectric layers 120. The patterning may, for example, be performed by a photolithography/etching process and/or some other suitable patterning process(es).

Also illustrated by the cross-sectional view 2300B of FIG. 23B, a pair of ISFET source/drain regions 106 and a pair of VRFET source/drain regions 108 are formed in the device layer 110a. The ISFET source/drain regions 106 are respectively on opposite sides of the solid ISFET gate electrode 116, and the VRFET source/drain regions 108 are respectively on opposite sides of the solid VRFET gate electrode 118. The ISFET and VRFET source/drain regions 106, 108 may, for example, be formed by selectively implanting dopants into the device layer 110a using ion implantation and/or some other suitable doping process.

Figure 23C:
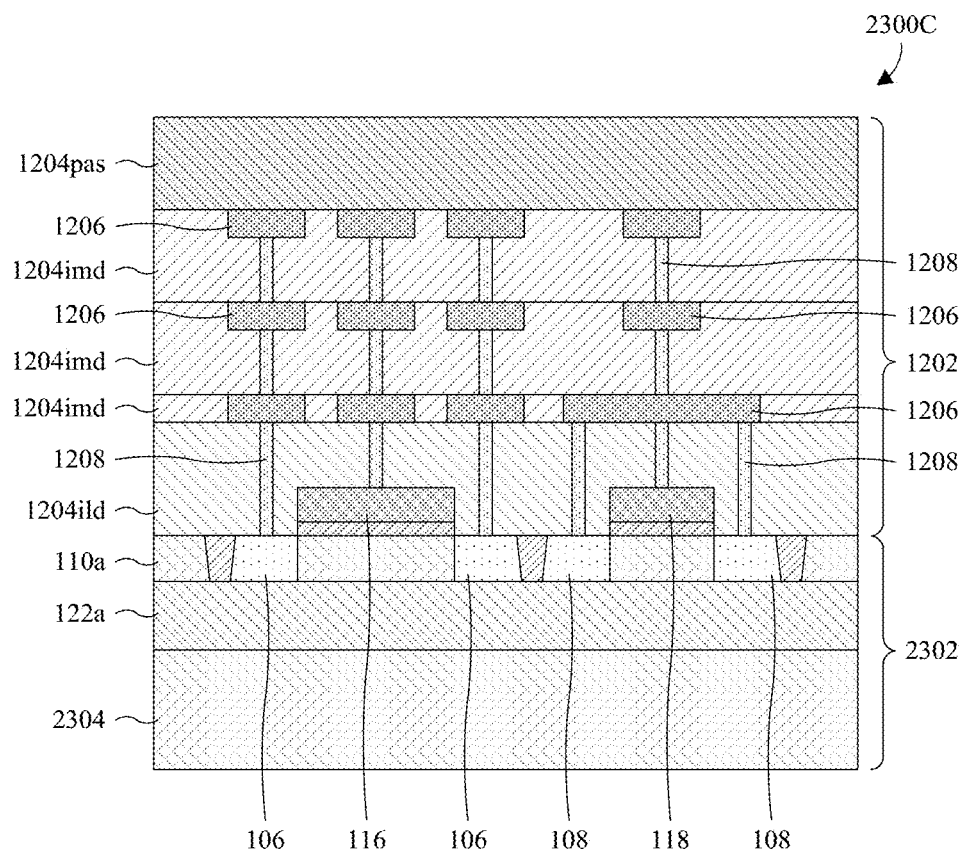

As illustrated by the cross-sectional view 2300C of FIG. 23C, an interconnect structure 1202 is formed over the SOI substrate 2302. The interconnect structure 1202 comprises an interlayer dielectric (ILD) layer 1204ild, a plurality of intermetal dielectric (IMD) layers 1204imd, and a frontside passivation layer 1204pas stacked over the SOI substrate 2302. Further, the interconnect structure 1202 comprises a plurality of wires 1206 and a plurality of vias 1208 stacked in the ILD, IMD, and frontside passivation layers 1204ild, 1204imd, 1204pas to define conductive paths. For example, the wires 1206 and the vias 1208 may define a conductive path electrically coupling the VRFET source/drain regions 108 and the solid VRFET gate electrode 118 together. As another example, while not illustrated, the wires 1206 and the vias 1208 may define a conductive path electrically coupling the ISFET source/drain regions 106 and the solid ISFET gate electrode 116 together in the same manner as the VRFET source/drain regions 108 and the solid VRFET gate electrode 118. This may, for example, be done for the DC/AC potentiometric readout methodology and/or the AC readout methodology discussed above.

In some embodiments, a process for forming the interconnect structure 1202 comprises: 1) forming the bottommost level of vias by a single damascene process; 2) forming the bottommost level of vias by the single damascene process; 3) forming subsequent levels of wires and vias by a dual damascene process; and 4) depositing a passivation layer over the topmost level of wires. Other processes are, however, amenable. In some embodiments, the single damascene process comprises: 1) depositing a dielectric layer (e.g., the ILD layer 1204ild or a bottommost one of the IMD layer 1204imd); 2) performing a planarization to flatten a top surface of the dielectric layer; 3) patterning the dielectric layer with openings for a single level of conductive features (e.g., a level of vias or a level of wires); 4) and filling the openings with conductive material to form the single level of conductive features. In some embodiments, the dual damascene process is the same as the single damascene processes, except the patterning forms openings for two levels of conductive features (e.g., a level of vias and a level of wires). Other single and/or dual damascene processes are, however, amenable.

Figure 23D:
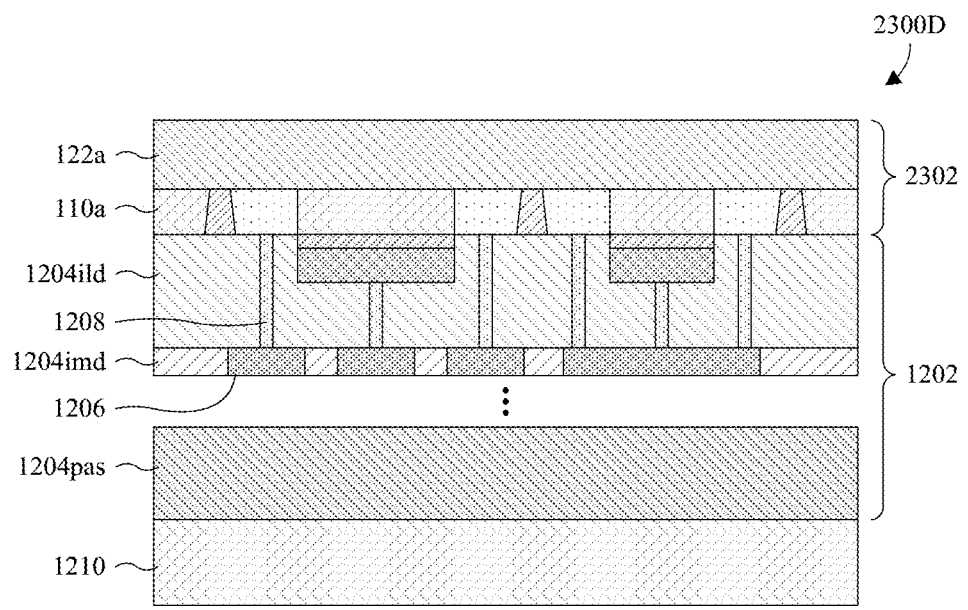

As illustrated by the cross-sectional view 2300D of FIG. 23D, the structure of FIG. 23C is flipped vertically and bonded to a carrier substrate 1210. The bonding may, for example, be performed by fusion bonding and/or some other suitable bonding process.

Also illustrated by the cross-sectional view 2300D of FIG. 23D, the SOI substrate 2302 is thinned to remove the bulk layer 2304 (see, e.g., FIG. 23C). The thinning may, for example, comprise mechanical grinding, a chemical mechanical polish (CMP), an etch back, some other suitable thinning process, or any combination of the foregoing.

Figure 23E:
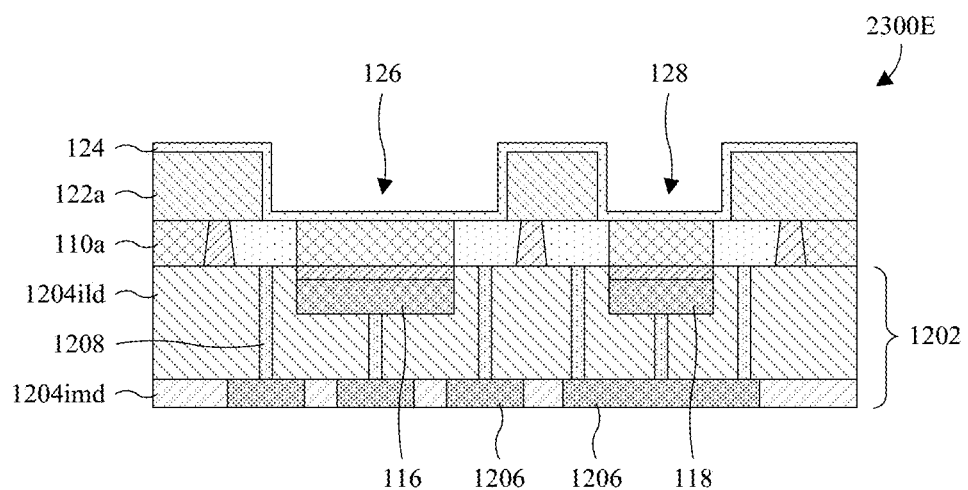

As illustrated by the cross-sectional view 2300E of FIG. 23E, the substrate dielectric layer 122a is patterned to form an ISFET well 126 and a VRFET well 128. The ISFET well 126 and the VRFET well 128 respectively overlie the solid ISFET gate electrode 116 and the solid VRFET gate electrode 118. Further, the ISFET well 126 and the VRFET well 128 expose a backside of the device layer 110a. The patterning may, for example, be performed by a photolithography/etching process and/or some other suitable patterning process.

Also illustrated by the cross-sectional view 2300E of FIG. 23E, a sensing layer 124 is formed lining the ISFET and VRFET wells 126, 128. In some embodiments, the sensing layer 124 is or comprises hafnium oxide, tantalum oxide, zirconium oxide, some other suitable high k dielectric(s), or any combination of the foregoing. In some embodiments, the sensing layer 124 is sensitive to a pH of a fluid and hence reacts to a pH of the fluid to change a surface potential difference at the sensing layer 124. The sensing layer 124 may, for example, be formed by vapor deposition and/or some other suitable deposition processes.

While not illustrated, in some embodiments, sensing probes are formed on the sensing layer 124 in the ISFET well 126, but not the VRFET well 128. An example of such a configuration is illustrated and described with regard to FIG. 2D.

Figure 23F:
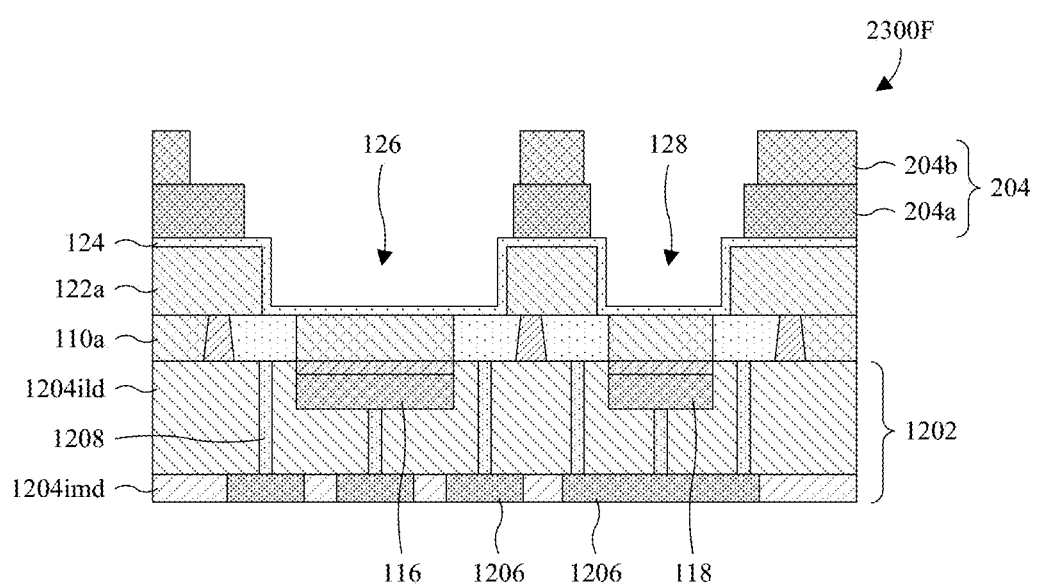

As illustrated by the cross-sectional view 2300F of FIG. 23F, a fluidic channel structure 204 is formed on or otherwise bonded to the sensing layer 124. The fluidic channel structure 204 defines fluidic channels individual to and respectively over the ISFET and VRFET wells 126, 128. In alternative embodiments, a single fluidic channel overlies the ISFET and VRFET wells 126, 128, an example of which is shown in FIG. 2F. The fluidic channel structure 204 may be or comprise, for example, PDMS, PMMA, some other suitable material(s), or any combination of the foregoing. In some embodiments, the fluidic channel structure 204 comprises a PDMS layer 204a and a PMMA layer 204b overlying the PDMS layer 204a.

While FIGS. 23A-23F are described with reference to a method, it will be appreciated that the structures shown in FIGS. 23A-23F are not limited to the method but rather may stand alone separate of the method. Further, while FIGS.

23A-23F are described as a series of acts, it will be appreciated that these acts are not limiting in that the order of the acts can be altered in other embodiments, and the methods disclosed are also applicable to other structures. In other embodiments, some acts that are illustrated and/or described may be omitted in whole or in part.

With reference to FIGS. 24A-24G, a series of cross-sectional views 2400A-2400G of some alternative embodiments of the method of FIGS. 23A-23F is provided in which a bulk substrate is used in place of the SOI substrate. The alternative method and variations thereof may, for example, be used to form the sensor in any one of the preceding figures.

Figure 24A:
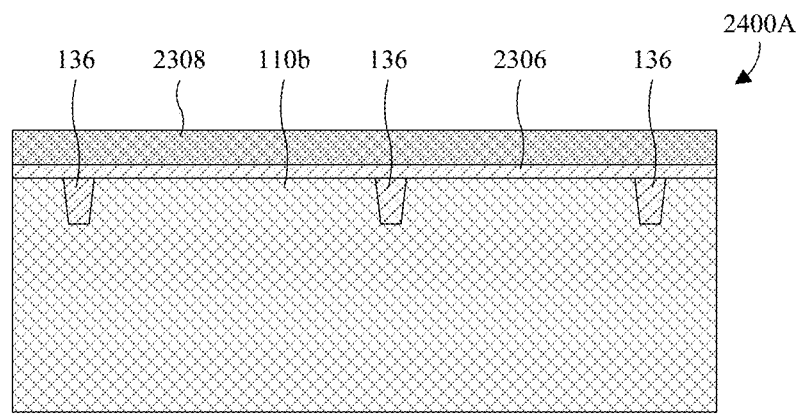
FIGS. 24A-24G illustrate a series of cross-sectional views of some alternative embodiments of the method of FIGS. 23A-23F using a bulk substrate.

As illustrated by the cross-sectional view 2400A of FIG. 24A, a bulk substrate 110b is provided. Further, a trench isolation structure 136, a dielectric layer 2306, and a conductive layer 2308 are formed on the bulk substrate 110b. The trench isolation structure 136, the dielectric layer 2306, and the conductive layer 2308 may, for example, be formed as described with regard to FIG. 23A. The bulk substrate 110b may, for example, be or comprise silicon and/or some other suitable semiconductor(s).

Figure 24B:
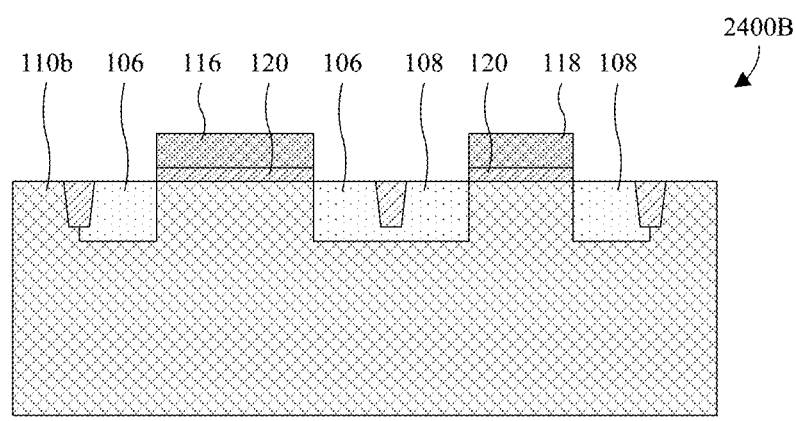

As illustrated by the cross-sectional view 2400B of FIG. 24B, the dielectric layer 2306 (see FIG. 24A) and the conductive layer 2308 (see FIG. 24B) are patterned to form a solid ISFET gate electrode 116 and a solid VRFET gate electrode 118 separated from the bulk substrate 110b by individual gate dielectric layers 120. The patterning may, for example, be performed by a photolithography/etching process and/or some other suitable patterning process(es).

Also illustrated by the cross-sectional view 2400B of FIG. 24B, a pair of ISFET source/drain regions 106 and a pair of VRFET source/drain regions 108 are formed in the bulk substrate 110b. The ISFET and VRFET source/drain regions 106, 108 may, for example, be formed by selectively implanting dopants into the bulk substrate 110b using ion implantation and/or some other suitable doping process.

Figure 24C:
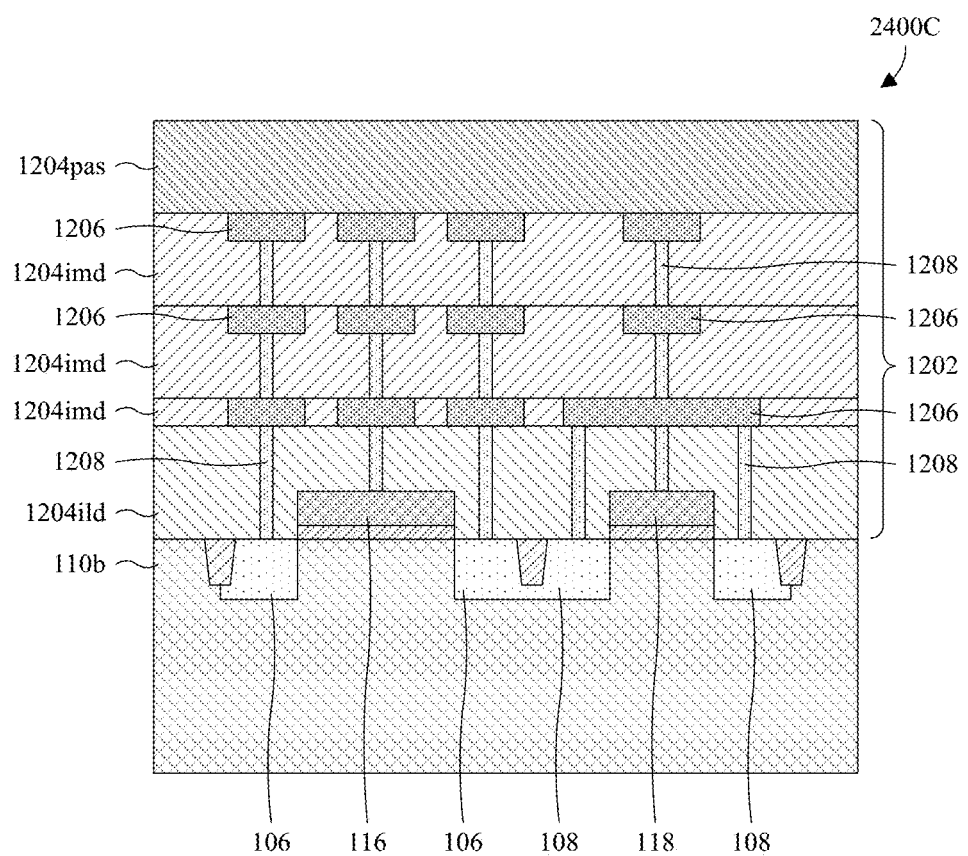

As illustrated by the cross-sectional view 2400C of FIG. 24C, an interconnect structure 1202 is formed over the bulk substrate 110b. The interconnect structure 1202 may, for example, be as illustrated and/or described with regard to FIG. 23C and/or may, for example, be formed as described with regard to FIG. 23C.

Figure 24D:
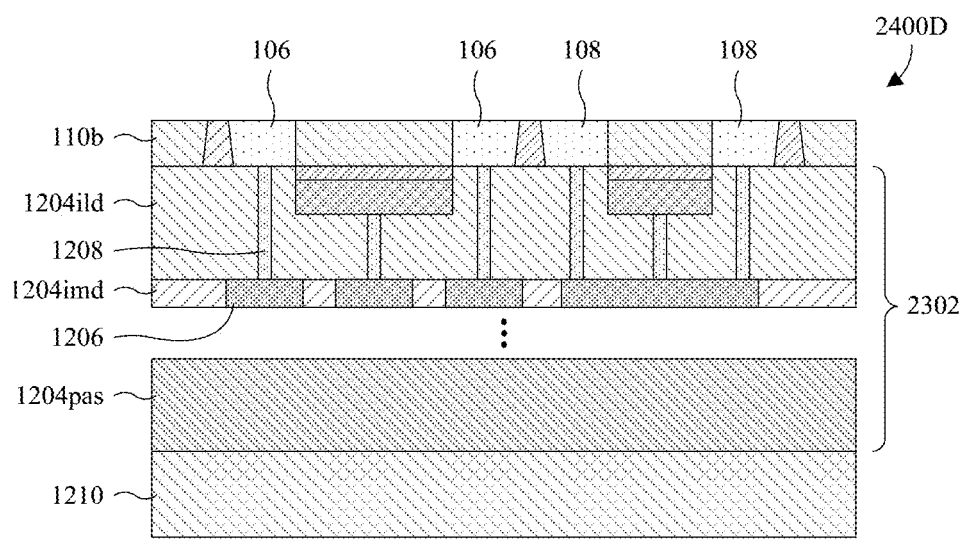

As illustrated by the cross-sectional view 2400D of FIG. 24D, the structure of FIG. 24C is flipped vertically and bonded to a carrier substrate 1210. The bonding may, for example, be performed by fusion bonding and/or some other suitable bonding process.

Also illustrated by the cross-sectional view 2400D of FIG. 24D, the bulk substrate 110b is thinned to expose the ISFET and VRFET source/drain regions 106, 108. The thinning may, for example, comprise mechanical grinding, a CMP, an etch back, some other suitable thinning process, or any combination of the foregoing.

Figure 24E:
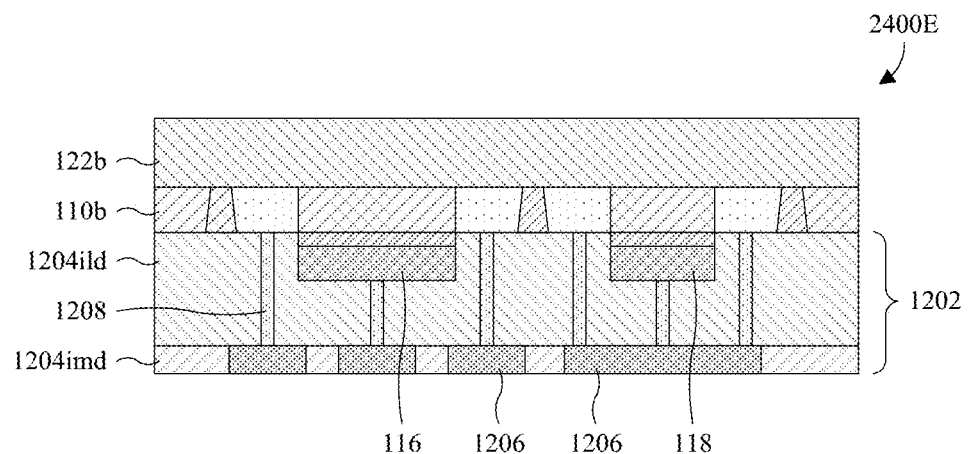

As illustrated by the cross-sectional view 2400E of FIG. 24E, a backside passivation layer 122b is formed on a backside of the bulk substrate 110b. The backside passivation layer 122b may, for example, be formed by vapor deposition, thermal oxidation, some other suitable deposition process(es), or any combination of the foregoing.

Figure 24F:
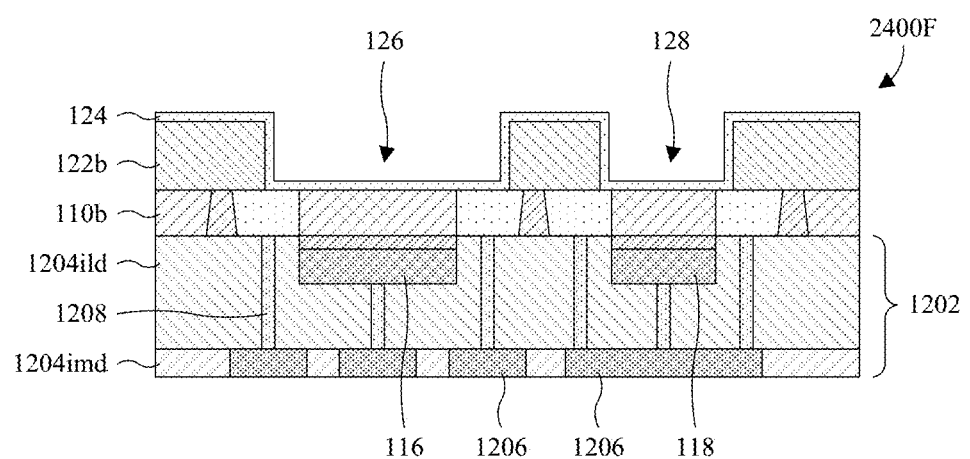

As illustrated by the cross-sectional view 2400F of FIG. 24F, the backside passivation layer 122b is patterned to form an ISFET well 126 and a VRFET well 128. The patterning may, for example, be performed by a photolithography/etching process and/or some other suitable patterning process.

Also illustrated by the cross-sectional view 2400F of FIG. 24F, a sensing layer 124 is formed lining the ISFET and VRFET wells 126, 128. The sensing layer 124 may, for example, be as described with regard to FIG. 23E.

While not illustrated, in some embodiments, sensing probes are formed on the sensing layer 124 in the ISFET well 126, but not the VRFET well 128. An example of such a configuration is illustrated and described with regard to FIG. 2D. Further, while not illustrated, in some embodiments, the sensing layer 124 is formed before the backside passivation layer 122b and the backside passivation layer 122b is formed over the sensing layer 124. Examples may, for example, be seen through reference to FIGS. 2A and 2B.

Figure 24G:
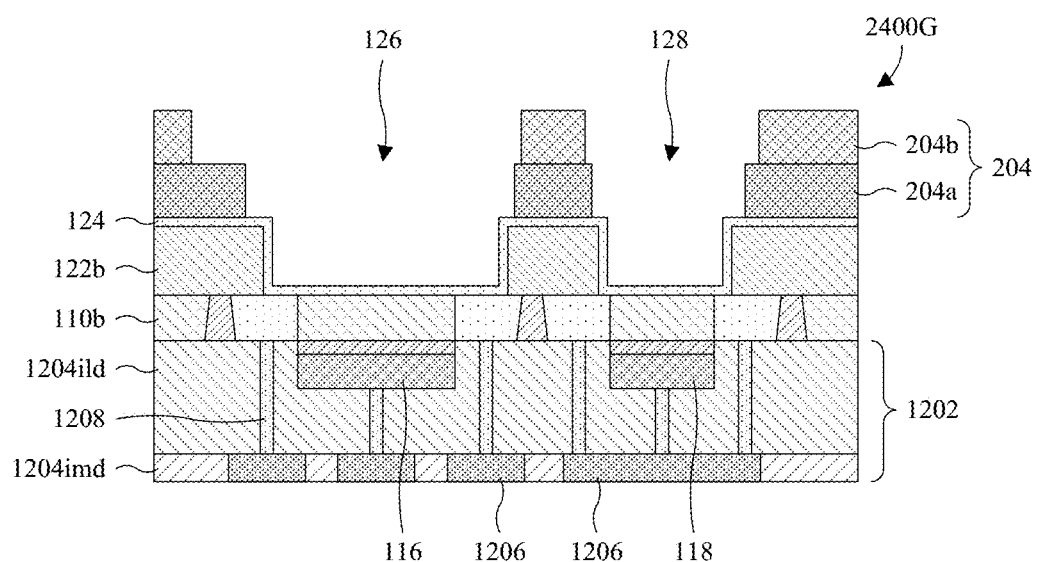

As illustrated by the cross-sectional view 2400G of FIG. 24G, a fluidic channel structure 204 is formed on or otherwise bonded to the sensing layer 124. The fluidic channel structure 204 may, for example, be as illustrated and described with regard to FIG. 23F and/or may, for example, be formed as described with regard to FIG. 23F.

While FIGS. 24A-24G are described with reference to a method, it will be appreciated that the structures shown in FIGS. 24A-24G are not limited to the method but rather may stand alone separate of the method. Further, while FIGS. 24A-24G are described as a series of acts, it will be appreciated that these acts are not limiting in that the order of the acts can be altered in other embodiments, and the methods disclosed are also applicable to other structures. In other embodiments, some acts that are illustrated and/or described may be omitted in whole or in part.

Figure 25:
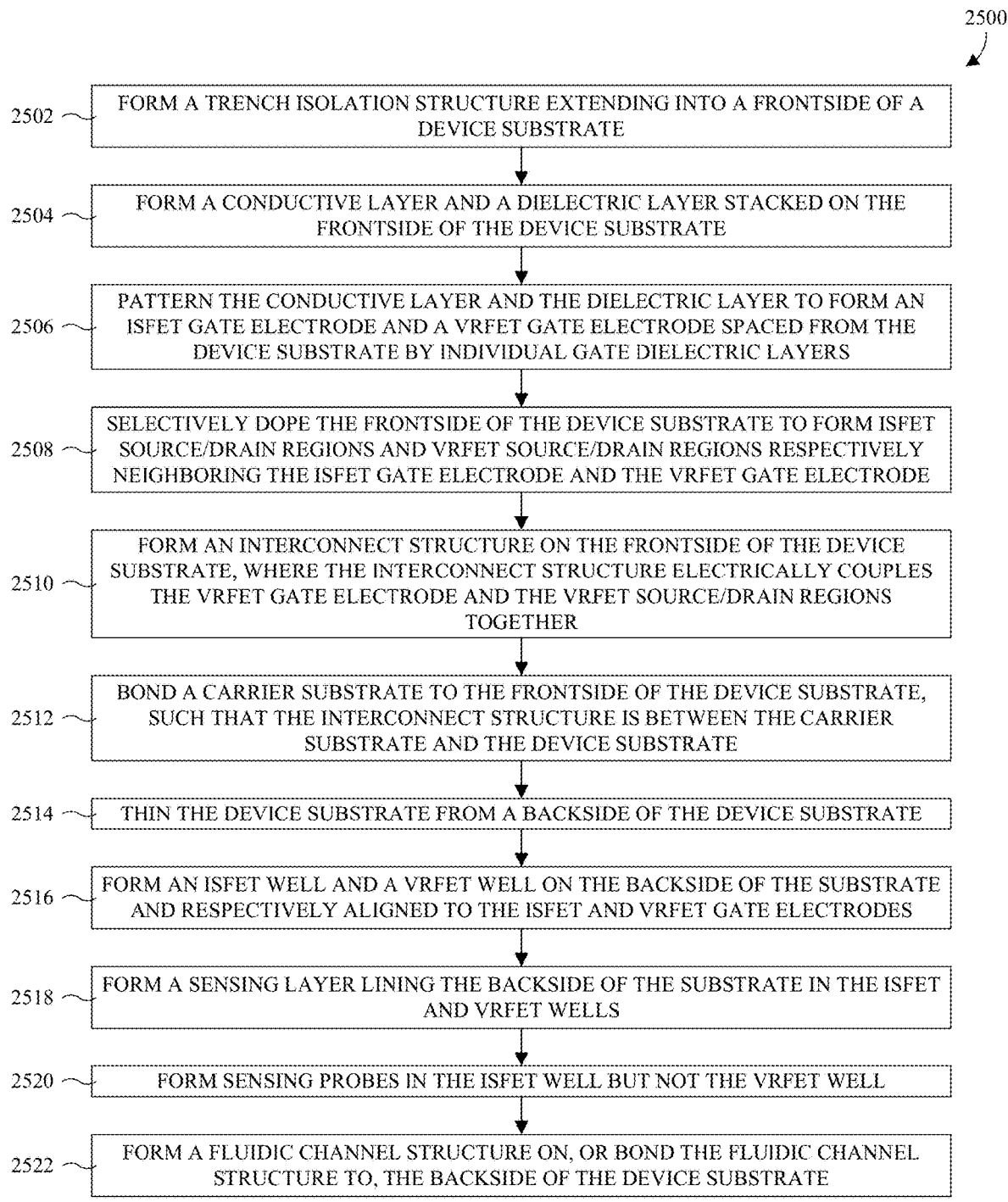
FIG. 25 illustrates a block diagram of some embodiments of the method of FIGS. 23A-23F and FIGS. 24A-24G.

With reference to FIG. 25, a block diagram 2500 of some embodiments of the method of FIGS. 23A-23F and FIGS. 24A-24G is provided.

At 2502, a trench isolation structure is formed extending into a frontside of a device substrate. See, for example, FIG. 23A or FIG. 24A.

At 2504, a conductive layer and a dielectric layer are formed stacked on the frontside of the device substrate. See, for example, FIG. 23A or FIG. 24A.

At 2506, the conductive layer and the dielectric layer are patterned to form an ISFET gate electrode and a VRFET gate electrode spaced from the device substrate by individual gate dielectric layers. See, for example, FIG. 23B or FIG. 24B.

At 2508, the frontside of the device substrate is selectively doped to form ISFET source/drain regions and VRFET source/drain regions respectively neighboring the ISFET gate electrode and the VRFET gate electrode. See, for example, FIG. 23B or FIG. 24B.

At 2510, an interconnect structure is formed on the frontside of the device substrate, where the interconnect structure electrically couples the VRFET gate electrode and the VRFET source/drain regions together. See, for example, FIG. 23C or FIG. 24C.

At 2512, a carrier substrate is bonded to the frontside of the device substrate, such that the interconnect structure is between the carrier substrate and the device substrate. See, for example, FIG. 23D or FIG. 24D.

At 2514, the device substrate is thinned from a backside of the device substrate. See, for example, FIG. 23D or FIG. 24D.

At 2516, an ISFET well and a VRFET well are formed on the backside of the substrate and respectively aligned to the ISFET and VRFET gate electrodes. See, for example, FIG. 23E or FIGS. 24E and 24F.

At 2518, a sensing layer is formed lining the backside of the substrate in the ISFET and VRFET wells. See, for example, FIG. 23E or FIG. 24F.

At 2520, sensing probes are formed in the ISFET well but not the VRFET well. This is not illustrated by FIGS. 23A-23F and FIGS. 24A-24G. However, an example of such sensing probes may, for example, be seen at FIG. 2D.

At 2522, a fluidic channel structure is formed on or bonded to the backside of the device substrate. See, for example, FIG. 23F or FIG. 24G.

While the method described by the block diagram 2500 is illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

In some embodiments, the present application provides a sensor including: a substrate including a pair of first source/drain regions and a pair of second source/drain regions; a first gate electrode and a second gate electrode underlying the substrate, wherein the first gate electrode is laterally between the first source/drain regions and the second gate electrode is laterally between the second source/drain regions; an interconnect structure underlying the substrate and defining conductive paths electrically coupling the second source/drain regions and the second gate electrode together; a passivation layer over the substrate and defining a first well and a second well, wherein the first and second wells respectively overlie the first and second gate electrodes; and a sensing layer lining the substrate in the first and second wells. In some embodiments, the sensor further includes a plurality of sensing probes in the first well and on the sensing layer, wherein the second well is devoid of sensing probes. In some embodiments, the interconnect structure further defines conductive paths interconnecting the first source/drain regions and the first gate electrode together. In some embodiments, the sensing layer includes hafnium oxide. In some embodiments, the first gate electrode and the first source/drain regions partially define an ISFET, wherein the second gate electrode and the second source/drain regions partially define a VRFET, wherein the ISFET and the VRFET have individual EDLs, and wherein the EDLs have a same thickness. In some embodiments, a separation between the first and second wells is about 0.1 micrometers to about 100 micrometers. In some embodiments, the substrate is fully depleted between the first source/drain regions and also between the second source/drain regions. In some embodiments, the first and second source/drain regions region have a same thickness as the substrate. In some embodiments, the sensor further includes a transimpedance amplifier having an input electrically coupled to one of the first source/drain regions. In some embodiments, the sensor further includes an array of field-effect transistors (FETs) on the substrate, wherein the array includes an N-type ion-sensitive FET (ISFET) and a P-type ISFET, and further includes an N-type voltage-reference FET (VRFET) and a P-type VRFET respectively neighboring the N-type ISFET and the P-type ISFET, wherein the N-type ISFET is at least partially defined by the first gate electrode and the first source/drain regions, and wherein the N-type VRFET is at least partially defined by the second gate electrode and the second source/drain regions.

In some embodiments, the present application provides a method including: forming a first gate electrode and a second gate electrode on a frontside of a substrate; doping the substrate to form a pair of first source/drain regions and a pair of second source/drain regions in the substrate, respectively bordering the first and second gate electrodes; forming an interconnect structure on the frontside of the substrate and electrically coupling the second source/drain regions and the second gate electrode together; forming a first well and a second well on a backside of the substrate, opposite the frontside and respectively aligned with the first and second gate electrodes, wherein the first and second wells expose the substrate; and depositing a sensing layer lining the substrate in the first and second wells. In some embodiments, the substrate is a SOI substrate, wherein the SOI substrate includes a bulk layer, a dielectric layer, and a device layer, wherein the first and second source/drain regions are formed in the device layer, and wherein the method further includes: after forming the interconnect structure, thinning the SOI substrate to remove the bulk layer and to expose the dielectric layer; and patterning the dielectric layer to form the first and second wells in the dielectric layer. In some embodiments, the method further includes: after forming the interconnect structure, thinning the substrate to expose the first and second source/drain regions; depositing a dielectric layer on the backside of the substrate; and patterning the dielectric layer to form the first and second wells in the dielectric layer. In some embodiments, the method further includes forming sensing probes on the sensing layer, localized to the first well.

In some embodiments, the present application provides another method including: providing a sensor including a reference electrode and an ISFET, wherein the ISFET includes a pair of source/drain regions and a body region in a substrate, and wherein the body region is fully depleted; applying a fluid to a sensing surface of the ISFET, wherein the fluid includes a target; biasing the reference electrode with a voltage having a same polarity as the target while the reference electrode is in the fluid, wherein the biasing induces formation of a channel in the body region and electrostatically repels the target towards the sensing surface; and measuring an impedance of the channel. In some embodiments, the body region has a doping concentration less than about $5 \times 10^{15}$ cm$^{-3}$. In some embodiments, the ISFET further includes a plurality of sensing probes on the sensing surface, and wherein the sensing probes selectively bind with the target. In some embodiments, the sensor further includes a second ISFET, wherein the second ISFET includes a plurality of second sensing probes on a second sensing surface of the second ISFET, and wherein the method further includes: applying the fluid to the second sensing surface of the ISFET, wherein the second sensing probes are non-selective for the target. In some embodiments, the reference electrode includes a pair of second source/drain regions and a second body region in the substrate, and further includes a gate electrode laterally between the second source/drain regions, and wherein the biasing includes applying the voltage to the gate electrode and the second source/drain regions. In some embodiments, the fluid has a first pH, and wherein the method further includes: after the measuring of the impedance, applying a second fluid to the sensing surface of the ISFET, wherein the second fluid has a second pH and includes the target; biasing the reference electrode with the voltage while the reference electrode is in the second fluid; and measuring a second impedance of the channel, wherein the second impedance is substantially the same as the impedance.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A sensor comprising:
   a substrate comprising a pair of first source/drain regions and a pair of second source/drain regions;
   a first gate electrode and a second gate electrode underlying the substrate, wherein the first gate electrode is laterally between the first source/drain regions and the second gate electrode is laterally between the second source/drain regions;
   an interconnect structure underlying the substrate and defining conductive paths electrically coupling the second source/drain regions and the second gate electrode together;
   a passivation layer over the substrate and defining a first well and a second well, wherein the first and second wells respectively overlie the first and second gate electrodes; and
   a sensing layer lining the substrate in the first and second wells;
   wherein the first gate electrode and the first source/drain regions partially define an ion-sensitive field-effect transistor (ISFET), and wherein the second gate electrode and the second source/drain regions partially define a voltage-reference field-effect transistor (VRFET).

2. The sensor according to claim 1, wherein the sensing layer comprises hafnium oxide.

3. The sensor according to claim 1, wherein the ISFET and the VRFET have individual electrical double layers (EDLs), and wherein the EDLs have a same thickness.

4. The sensor according to claim 1, wherein a separation between the first and second wells is about 0.1 micrometers to about 100 micrometers.

5. The sensor according to claim 1, wherein the substrate is fully depleted between the first source/drain regions and also between the second source/drain regions.

6. The sensor according to claim 1, wherein the first and second source/drain regions have a same thickness as the substrate.

7. The sensor according to claim 1, wherein the pair of first source/drain regions neighbors the pair of second source/drain regions, and wherein the interconnect structure electrically shorts the second source/drain regions together.

8. The sensor according to claim 1, wherein the first well borders the second well and overlies a portion of the substrate separating the first source/drain regions, wherein the second well overlies a portion of the substrate separating the second source/drain regions, wherein the interconnect structure electrically shorts the second source/drain regions together, but not the first source/drain regions together, and wherein the sensing layer overlies the substrate and directly contacts the substrate at each of the first and second wells.

9. A sensor comprising:
   a substrate comprising a pair of first source/drain regions and a pair of second source/drain regions;
   a first gate electrode and a second gate electrode underlying the substrate, wherein the first gate electrode is laterally between the first source/drain regions and the second gate electrode is laterally between the second source/drain regions;
   an interconnect structure underlying the substrate and defining conductive paths electrically coupling the second source/drain regions and the second gate electrode together;
   a passivation layer over the substrate and defining a first well and a second well, wherein the first and second wells respectively overlie the first and second gate electrodes; and
   a sensing layer lining the substrate in the first and second wells;
   wherein the pair of first source/drain regions neighbors the pair of second source/drain regions, and wherein the interconnect structure electrically shorts the second source/drain regions together.

10. The sensor according to claim 9, wherein the first source/drain regions and the first gate electrode partially define an ion-sensitive field-effect transistor (ISFET), and wherein the second source/drain regions and the second gate electrode partially define a voltage-reference field-effect transistor (VRFET).

11. The sensor according to claim 9, wherein the substrate is undoped between the first source/drain regions and between the second source/drain regions.

12. The sensor according to claim 9, wherein the first source/drain regions and the second source/drain regions have individual heights equal to a thickness of the substrate.

13. The sensor according to claim 9, further comprising:
    a current-to-voltage converter; and
    a sampling switch selectively electrically coupling an input of the current-to-voltage converter to one of the first source/drain regions.

14. The sensor according to claim 9, wherein the first source/drain regions are electrically isolated from each other.

15. A sensor comprising:
    a substrate comprising a pair of first source/drain regions and a pair of second source/drain regions;
    a first gate electrode and a second gate electrode underlying the substrate, wherein the first gate electrode is laterally between the first source/drain regions and the second gate electrode is laterally between the second source/drain regions;
    an interconnect structure underlying the substrate and defining conductive paths electrically coupling the second source/drain regions and the second gate electrode together;
    a passivation layer over the substrate and defining a first well and a second well, wherein the first and second wells respectively overlie the first and second gate electrodes; and
    a sensing layer lining the substrate in the first and second wells;
    wherein the first well borders the second well and overlies a portion of the substrate separating the first source/drain regions, wherein the second well overlies a portion of the substrate separating the second source/drain regions, wherein the interconnect structure electrically shorts the second source/drain regions together, but not the first source/drain regions together, and wherein the sensing layer overlies the substrate and directly contacts the substrate at each of the first and second wells.

16. The sensor according to claim 15, wherein the portions of the substrate separating the first and second source regions have a doping concentration less than about $5\times10^{15}$ atoms per cubic centimeter.

17. The sensor according to claim 15, wherein the first source/drain regions and the first gate electrode partially define a first n-channel field-effect transistor (FET), and wherein the second source/drain regions partially define a second n-channel FET bordering the first n-channel FET.

18. The sensor according to claim 15, wherein the sensing layer comprises a high k dielectric.

19. The sensor according to claim 15, wherein the first gate electrode and the first source/drain regions partially define an ion-sensitive field-effect transistor (ISFET), wherein the second gate electrode and the second source/drain regions partially define a voltage-reference field-effect transistor (VRFET), wherein the ISFET and the VRFET have individual electrical double layers (EDLs), and wherein the EDLs have a same thickness.

20. The sensor according to claim 15, wherein a separation between the first and second wells is about 0.1 micrometers to about 100 micrometers.

\* \* \* \* \*